US011833297B2

(12) United States Patent
Jafari et al.

(10) Patent No.: US 11,833,297 B2
(45) Date of Patent: *Dec. 5, 2023

(54) METHODS AND SYSTEMS FOR ADAPTIVE BASE FLOW AND LEAK COMPENSATION

(71) Applicant: Covidien LP, Mansfield, MA (US)

(72) Inventors: Mehdi M. Jafari, Laguna Hills, CA (US); Milenko Masic, Carlsbad, CA (US); Rhomere S. Jimenez, Chula Vista, CA (US); Jeffrey K Aviano, Escondido, CA (US); Edward R. McCoy, Vista, CA (US)

(73) Assignee: Covidien LP, Mansfield, MA (US)

( * ) Notice: Subject to any disclaimer, the term of this patent is extended or adjusted under 35 U.S.C. 154(b) by 624 days.

This patent is subject to a terminal disclaimer.

(21) Appl. No.: 16/890,341

(22) Filed: Jun. 2, 2020

(65) Prior Publication Data

US 2020/0297950 A1    Sep. 24, 2020

Related U.S. Application Data

(63) Continuation of application No. 15/358,519, filed on Nov. 22, 2016, now Pat. No. 10,709,854, which is a (Continued)

(51) Int. Cl.
*A61M 16/00* (2006.01)
*A61M 16/08* (2006.01)

(52) U.S. Cl.
CPC ...... *A61M 16/0003* (2014.02); *A61M 16/026* (2017.08); *A61M 16/0875* (2013.01); (Continued)

(58) Field of Classification Search
CPC ............ A61M 16/0003; A61M 16/021; A61M 16/022; A61M 16/024; A61M 16/026; (Continued)

(56) References Cited

U.S. PATENT DOCUMENTS 3,444,857 A    5/1969   Godel
3,481,333 A    12/1969  Garrison
(Continued)

FOREIGN PATENT DOCUMENTS

WO    WO 2003/055552    7/2003
WO    WO 2006137784     12/2006
WO    WO 2007/102866    9/2007

OTHER PUBLICATIONS

7200 Series Ventilator, Options, and Accessories: Operator's Manual. Nellcor Puritan Bennett, Part No. 22300 A, Sep. 1990, pp. 1-196.
(Continued)

*Primary Examiner* — Kathryn E Ditmer

(57) ABSTRACT

This disclosure describes systems and methods for providing adaptive base flow scheduling during ventilation of a patient to optimize patient-machine synchrony and accuracy of estimated exhaled as well as inhaled tidal volumes. Further, this disclosure describes systems and methods for providing adaptive inspiratory trigger threshold scheduling during the adaptive base flow scheduling. Further still, this disclosure describes systems and methods for determining an estimated leak flow and adjusting the adaptive base flow scheduling and the adaptive inspiratory trigger threshold scheduling based on the estimated leak flow. Moreover, this disclosure describes systems and methods for determining a change in the estimated leak flow and adjusting the adaptive base flow scheduling and the adaptive inspiratory trigger threshold scheduling based on the change in the estimated leak flow.

19 Claims, 5 Drawing Sheets

Related U.S. Application Data continuation of application No. 13/341,957, filed on Dec. 31, 2011, now Pat. No. 9,498,589.

(52) U.S. Cl.
CPC ..... *A61M 16/0063* (2014.02); *A61M 16/0833* (2014.02); *A61M 2016/0018* (2013.01); *A61M 2016/0021* (2013.01); *A61M 2016/0027* (2013.01); *A61M 2016/0033* (2013.01); *A61M 2016/0036* (2013.01); *A61M 2016/0039* (2013.01); *A61M 2016/0042* (2013.01); *A61M 2205/15* (2013.01); *A61M 2205/505* (2013.01); *A61M 2205/583* (2013.01); *A61M 2230/40* (2013.01)

(58) Field of Classification Search
CPC .... A61M 2016/018; A61M 2016/0021; A61M 2016/0027; A61M 2016/003; A61M 2016/0033; A61M 2016/0036; A61M 2016/0039; A61M 2016/0042
See application file for complete search history.

(56) References Cited

U.S. PATENT DOCUMENTS

| | | | |
|---|---|---|---|
| 3,485,243 A | 12/1969 | Bird et al. |
| 3,584,621 A | 6/1971 | Bird et al. |
| 3,586,021 A | 6/1971 | McGuinness |
| 3,633,576 A | 1/1972 | Gorsuch |
| 3,662,751 A | 5/1972 | Barkalow et al. |
| 3,664,370 A | 5/1972 | Warnow |
| 3,669,108 A | 6/1972 | Sundblom et al. |
| 3,688,794 A | 9/1972 | Bird et al. |
| 3,695,263 A | 10/1972 | Kipling |
| 3,741,208 A | 6/1973 | Jonsson et al. |
| 3,753,436 A | 8/1973 | Bird et al. |
| 3,756,229 A | 9/1973 | Ollivier |
| 3,768,468 A | 10/1973 | Cox |
| 3,789,837 A | 2/1974 | Philips et al. |
| 3,827,433 A | 8/1974 | Shannon |
| 3,834,382 A | 9/1974 | Lederman et al. |
| 3,869,771 A | 3/1975 | Bollinger |
| 3,889,669 A | 6/1975 | Weigl |
| 3,889,670 A | 6/1975 | Loveland et al. |
| 3,896,800 A | 7/1975 | Cibulka |
| 3,903,881 A | 9/1975 | Weigl |
| 3,905,362 A | 9/1975 | Eyrick et al. |
| 3,908,987 A | 9/1975 | Boehringer |
| 3,910,261 A | 10/1975 | Ragsdale et al. |
| 3,961,627 A | 6/1976 | Ernst et al. |
| 3,976,052 A | 8/1976 | Junginger et al. |
| 3,976,065 A | 8/1976 | Durkan |
| 3,981,301 A | 9/1976 | Warnow et al. |
| 4,003,377 A | 1/1977 | Dahl |
| 4,020,834 A | 5/1977 | Bird |
| 4,029,120 A | 6/1977 | Christianson |
| 4,044,763 A | 8/1977 | Bird |
| 4,050,458 A | 9/1977 | Friend |
| 4,057,059 A | 11/1977 | Reid, Jr. et al. |
| 4,060,078 A | 11/1977 | Bird |
| 4,082,093 A | 4/1978 | Fry et al. |
| 4,121,578 A | 10/1978 | Torzala |
| 4,155,357 A | 5/1979 | Dahl |
| 4,164,219 A | 8/1979 | Bird |
| 4,197,843 A | 4/1980 | Bird |
| 4,197,856 A | 4/1980 | Northrop |
| 4,206,754 A | 6/1980 | Cox et al. |
| 4,211,221 A | 7/1980 | Schwanbom et al. |
| 4,211,239 A | 7/1980 | Raemer et al. |
| 4,227,523 A | 10/1980 | Warnow et al. |
| 4,232,666 A | 11/1980 | Savelli et al. |
| 4,241,756 A | 12/1980 | Bennett et al. |
| 4,245,633 A | 1/1981 | Erceg |
| 4,265,237 A | 5/1981 | Schwanbom et al. |
| 4,267,827 A | 5/1981 | Racher et al. |
| 4,275,722 A | 6/1981 | Sorensen |
| 4,281,651 A | 8/1981 | Cox |
| 4,285,340 A | 8/1981 | Gezari et al. |
| 4,320,754 A | 3/1982 | Watson et al. |
| 4,323,064 A | 4/1982 | Hoenig et al. |
| 4,340,044 A | 7/1982 | Levy et al. |
| 4,351,328 A | 9/1982 | Bodai |
| 4,351,329 A | 9/1982 | Ellestad et al. |
| 4,351,344 A | 9/1982 | Stenzler |
| 4,401,115 A | 8/1983 | Monnier |
| 4,417,573 A | 11/1983 | De Vries |
| 4,436,090 A | 3/1984 | Darling |
| 4,457,304 A | 7/1984 | Molnar et al. |
| 4,459,982 A | 7/1984 | Fry |
| 4,459,983 A | 7/1984 | Beyreuther et al. |
| 4,462,397 A | 7/1984 | Suzuki |
| 4,502,481 A | 3/1985 | Christian |
| 4,527,557 A | 7/1985 | DeVries et al. |
| 4,539,984 A | 9/1985 | Kiszel et al. |
| 4,554,916 A | 11/1985 | Watt |
| 4,558,710 A | 12/1985 | Eichler |
| 4,566,450 A | 1/1986 | Brossman, Jr. |
| 4,596,246 A | 6/1986 | Lyall |
| 4,598,706 A | 7/1986 | Darowski et al. |
| 4,608,976 A | 9/1986 | Suchy |
| 4,611,591 A | 9/1986 | Inui et al. |
| 4,612,928 A | 9/1986 | Tiep et al. |
| 4,622,976 A | 11/1986 | Timpe et al. |
| 4,640,277 A | 2/1987 | Meyer et al. |
| 4,648,407 A | 3/1987 | Sackner |
| 4,651,731 A | 3/1987 | Vicenzi et al. |
| 4,699,137 A | 10/1987 | Schroeder |
| RE32,553 E | 12/1987 | Bennett et al. |
| 4,712,580 A | 12/1987 | Gilman et al. |
| 4,727,871 A | 3/1988 | Smargiassi et al. |
| 4,747,403 A | 5/1988 | Gluck et al. |
| 4,752,089 A | 6/1988 | Carter |
| 4,757,824 A | 7/1988 | Chaumet |
| 4,766,894 A | 8/1988 | Legrand et al. |
| 4,796,618 A | 1/1989 | Garraffa |
| 4,813,409 A | 3/1989 | Ismach |
| 4,821,709 A | 4/1989 | Jensen |
| 4,877,023 A | 10/1989 | Zalkin |
| 4,889,116 A | 12/1989 | Taube |
| 4,921,642 A | 5/1990 | LaTorraca |
| 4,924,862 A | 5/1990 | Levinson |
| 4,954,799 A | 9/1990 | Kumar |
| 4,957,107 A | 9/1990 | Sipin |
| 4,981,295 A | 1/1991 | Belman et al. |
| 4,982,735 A | 1/1991 | Yagata et al. |
| 4,991,576 A | 2/1991 | Henkin et al. |
| 4,993,269 A | 2/1991 | Guillaume et al. |
| 5,000,173 A | 3/1991 | Zalkin et al. |
| 5,002,050 A | 3/1991 | McGinnis |
| 5,007,420 A | 4/1991 | Bird |
| 5,016,626 A | 5/1991 | Jones |
| 5,020,532 A | 6/1991 | Mahoney et al. |
| 5,057,822 A | 10/1991 | Hoffman |
| 5,063,925 A | 11/1991 | Frank et al. |
| 5,065,746 A | 11/1991 | Steen |
| 5,067,487 A | 11/1991 | Bauman |
| 5,072,728 A | 12/1991 | Pasternack |
| 5,072,729 A | 12/1991 | DeVries |
| 5,072,737 A | 12/1991 | Goulding |
| 5,099,837 A | 3/1992 | Russel, Sr. et al. |
| 5,109,838 A | 5/1992 | Elam |
| 5,127,400 A | 7/1992 | DeVries et al. |
| 5,134,995 A | 8/1992 | Gruenke et al. |
| 5,148,802 A | 9/1992 | Sanders et al. |
| 5,150,291 A | 9/1992 | Cummings et al. |
| 5,154,167 A | 10/1992 | Hepburn |
| 5,158,569 A | 10/1992 | Strickland et al. |
| 5,161,525 A | 11/1992 | Kimm et al. |
| 5,165,397 A | 11/1992 | Arp |
| 5,168,868 A | 12/1992 | Hicks |
| 5,178,155 A | 1/1993 | Mault |
| 5,222,491 A | 6/1993 | Thomas |
| 5,237,987 A | 8/1993 | Anderson et al. |

(56) References Cited

U.S. PATENT DOCUMENTS

| | | | |
|---|---|---|---|
| 5,239,995 | A | 8/1993 | Estes et al. |
| 5,255,675 | A | 10/1993 | Kolobow |
| 5,259,373 | A | 11/1993 | Gruenke et al. |
| 5,269,293 | A | 12/1993 | Loser et al. |
| 5,271,389 | A | 12/1993 | Isaza et al. |
| 5,277,175 | A | 1/1994 | Riggs et al. |
| 5,279,549 | A | 1/1994 | Ranford |
| 5,299,568 | A | 4/1994 | Forare et al. |
| 5,301,667 | A | 4/1994 | McGrail et al. |
| 5,301,921 | A | 4/1994 | Kumar |
| 5,303,698 | A | 4/1994 | Tobia et al. |
| 5,303,699 | A | 4/1994 | Bonassa et al. |
| 5,309,901 | A | 5/1994 | Beaussant |
| 5,313,937 | A | 5/1994 | Zdrojkowski |
| 5,315,989 | A | 5/1994 | Tobia |
| 5,316,009 | A | 5/1994 | Yamada |
| 5,318,487 | A | 6/1994 | Golen et al. |
| 5,319,540 | A | 6/1994 | Isaza et al. |
| 5,323,772 | A | 6/1994 | Linden et al. |
| 5,325,861 | A | 7/1994 | Goulding |
| 5,331,995 | A | 7/1994 | Westfall et al. |
| 5,333,606 | A | 8/1994 | Schneider et al. |
| 5,335,654 | A | 8/1994 | Rapoport |
| 5,339,807 | A | 8/1994 | Carter |
| 5,343,857 | A | 9/1994 | Schneider et al. |
| 5,343,858 | A | 9/1994 | Winefordner et al. |
| 5,351,522 | A | 10/1994 | Lura |
| 5,357,946 | A | 10/1994 | Kee et al. |
| 5,360,000 | A | 11/1994 | Carter |
| 5,368,019 | A | 11/1994 | LaTorraca |
| 5,368,021 | A | 11/1994 | Beard et al. |
| 5,373,842 | A * | 12/1994 | Olsson ............... A61M 16/1015 128/204.26 |
| 5,383,449 | A | 1/1995 | Forare et al. |
| 5,385,142 | A | 1/1995 | Brady et al. |
| 5,390,666 | A | 2/1995 | Kimm et al. |
| 5,398,677 | A | 3/1995 | Smith |
| 5,401,135 | A | 3/1995 | Stoen et al. |
| 5,402,796 | A | 4/1995 | Packer et al. |
| 5,404,871 | A | 4/1995 | Goodman et al. |
| 5,407,174 | A | 4/1995 | Kumar |
| 5,413,110 | A | 5/1995 | Cummings et al. |
| 5,429,123 | A | 7/1995 | Shaffer et al. |
| 5,433,193 | A | 7/1995 | Sanders et al. |
| 5,438,980 | A | 8/1995 | Phillips |
| 5,443,075 | A | 8/1995 | Holscher |
| 5,452,714 | A | 9/1995 | Anderson et al. |
| 5,458,137 | A | 10/1995 | Axe et al. |
| 5,467,766 | A | 11/1995 | Ansite et al. |
| 5,479,920 | A | 1/1996 | Piper et al. |
| 5,484,270 | A | 1/1996 | Adahan |
| 5,487,383 | A | 1/1996 | Levinson |
| 5,492,113 | A | 2/1996 | Estes et al. |
| 5,494,028 | A | 2/1996 | DeVries et al. |
| 5,497,767 | A | 3/1996 | Olsson et al. |
| 5,503,140 | A | 4/1996 | Winefordner et al. |
| 5,503,146 | A | 4/1996 | Froehlich et al. |
| 5,507,282 | A | 4/1996 | Younes |
| 5,509,406 | A | 4/1996 | Kock et al. |
| 5,513,631 | A | 5/1996 | McWilliams |
| 5,517,983 | A | 5/1996 | Deighan et al. |
| 5,520,071 | A | 5/1996 | Jones |
| 5,524,615 | A | 6/1996 | Power |
| 5,531,221 | A | 7/1996 | Power |
| 5,535,738 | A | 7/1996 | Estes et al. |
| 5,540,220 | A | 7/1996 | Gropper et al. |
| 5,542,415 | A | 8/1996 | Brady |
| 5,542,416 | A | 8/1996 | Chalvignac |
| 5,544,674 | A | 8/1996 | Kelly |
| 5,546,935 | A | 8/1996 | Champeau |
| 5,549,106 | A | 8/1996 | Gruenke et al. |
| 5,549,655 | A | 8/1996 | Erickson |
| 5,551,418 | A | 9/1996 | Estes et al. |
| 5,551,419 | A | 9/1996 | Froehlich et al. |
| 5,555,880 | A | 9/1996 | Winter et al. |
| 5,564,416 | A | 10/1996 | Jones |
| 5,568,910 | A | 10/1996 | Koehler et al. |
| 5,575,283 | A | 11/1996 | Sjoestrand |
| 5,582,163 | A | 12/1996 | Bonassa |
| 5,596,984 | A | 1/1997 | O'Mahoney et al. |
| 5,598,838 | A | 2/1997 | Servidio et al. |
| 5,603,315 | A | 2/1997 | Sasso, Jr. |
| 5,606,968 | A | 3/1997 | Mang |
| 5,615,669 | A | 4/1997 | Olsson et al. |
| 5,617,847 | A | 4/1997 | Howe |
| 5,630,411 | A | 5/1997 | Holscher |
| 5,632,269 | A | 5/1997 | Zdrojkowski |
| 5,632,270 | A | 5/1997 | O'Mahony et al. |
| 5,645,048 | A | 7/1997 | Brodsky et al. |
| 5,645,053 | A | 7/1997 | Remmers et al. |
| 5,647,345 | A | 7/1997 | Saul |
| 5,647,351 | A * | 7/1997 | Weismann ............ A61M 16/204 128/204.26 |
| 5,651,360 | A | 7/1997 | Tobia |
| 5,657,750 | A | 8/1997 | Colman et al. |
| 5,660,171 | A | 8/1997 | Kimm et al. |
| 5,662,099 | A | 9/1997 | Tobia et al. |
| 5,664,560 | A | 9/1997 | Merrick et al. |
| 5,664,562 | A | 9/1997 | Bourdon |
| 5,671,767 | A | 9/1997 | Kelly |
| 5,672,041 | A | 9/1997 | Ringdahl et al. |
| 5,673,689 | A | 10/1997 | Power |
| 5,678,537 | A | 10/1997 | Bathe et al. |
| 5,683,232 | A | 11/1997 | Adahan |
| 5,692,497 | A | 12/1997 | Schnitzer et al. |
| 5,697,363 | A | 12/1997 | Hart |
| 5,701,883 | A | 12/1997 | Hete et al. |
| 5,701,889 | A | 12/1997 | Danon |
| 5,706,799 | A | 1/1998 | Imai et al. |
| 5,715,812 | A | 2/1998 | Deighan et al. |
| 5,720,277 | A | 2/1998 | Olsson et al. |
| 5,727,562 | A | 3/1998 | Beck |
| 5,735,267 | A | 4/1998 | Tobia |
| 5,738,090 | A | 4/1998 | Lachmann et al. |
| 5,740,796 | A | 4/1998 | Skog |
| 5,752,509 | A | 5/1998 | Lachmann et al. |
| 5,762,480 | A | 6/1998 | Adahan |
| 5,769,072 | A | 6/1998 | Olsson et al. |
| 5,771,884 | A | 6/1998 | Yarnall et al. |
| 5,791,339 | A | 8/1998 | Winter |
| 5,794,614 | A | 8/1998 | Gruenke et al. |
| 5,794,615 | A | 8/1998 | Estes |
| 5,794,986 | A | 8/1998 | Gansel et al. |
| 5,797,393 | A | 8/1998 | Kohl |
| 5,803,064 | A | 9/1998 | Phelps et al. |
| 5,803,065 | A | 9/1998 | Zdrojkowski et al. |
| 5,803,066 | A | 9/1998 | Rapoport et al. |
| 5,813,399 | A | 9/1998 | Isaza et al. |
| 5,823,179 | A | 10/1998 | Grychowski et al. |
| 5,823,187 | A | 10/1998 | Estes et al. |
| 5,826,575 | A | 10/1998 | Lall |
| 5,829,441 | A | 11/1998 | Kidd et al. |
| 5,845,636 | A | 12/1998 | Gruenke et al. |
| 5,857,458 | A | 1/1999 | Tham et al. |
| 5,864,938 | A | 2/1999 | Gansel et al. |
| 5,865,168 | A | 2/1999 | Isaza |
| 5,865,173 | A | 2/1999 | Froehlich |
| 5,868,133 | A | 2/1999 | DeVries et al. |
| 5,875,783 | A | 3/1999 | Kullik |
| 5,876,352 | A | 3/1999 | Weismann |
| 5,881,717 | A | 3/1999 | Isaza |
| 5,881,722 | A | 3/1999 | DeVries et al. |
| 5,881,723 | A | 3/1999 | Wallace et al. |
| 5,884,622 | A | 3/1999 | Younes |
| 5,884,623 | A | 3/1999 | Winter |
| 5,901,704 | A | 5/1999 | Estes et al. |
| 5,904,141 | A | 5/1999 | Estes et al. |
| 5,909,731 | A | 6/1999 | O'Mahony et al. |
| 5,915,379 | A | 6/1999 | Wallace et al. |
| 5,915,380 | A | 6/1999 | Wallace et al. |
| 5,915,381 | A | 6/1999 | Nord |
| 5,915,382 | A | 6/1999 | Power |
| 5,918,597 | A | 7/1999 | Jones et al. |
| 5,921,238 | A | 7/1999 | Bourdon |

(56) References Cited

U.S. PATENT DOCUMENTS

| | | |
|---|---|---|
| 5,921,920 A | 7/1999 | Marshall et al. |
| 5,927,274 A | 7/1999 | Servidio et al. |
| 5,931,162 A | 8/1999 | Christian |
| 5,934,274 A | 8/1999 | Merrick et al. |
| 5,937,856 A | 8/1999 | Jonasson et al. |
| 5,941,846 A | 8/1999 | Duffy et al. |
| 5,957,130 A | 9/1999 | Krahbichler et al. |
| 5,970,975 A | 10/1999 | Estes et al. |
| 5,983,891 A | 11/1999 | Fukunaga |
| 6,010,459 A | 1/2000 | Silkoff et al. |
| 6,024,089 A | 2/2000 | Wallace et al. |
| 6,029,664 A | 2/2000 | Zdrojkowski et al. |
| 6,041,777 A | 3/2000 | Faithfull et al. |
| 6,041,780 A | 3/2000 | Richard et al. |
| 6,042,550 A | 3/2000 | Haryadi et al. |
| 6,044,841 A | 4/2000 | Verdun et al. |
| 6,047,860 A | 4/2000 | Sanders |
| 6,055,981 A | 5/2000 | Laswick et al. |
| 6,066,101 A | 5/2000 | Johnson et al. |
| 6,067,984 A | 5/2000 | Piper |
| 6,073,630 A | 6/2000 | Adahan |
| 6,076,519 A | 6/2000 | Johnson |
| 6,076,523 A | 6/2000 | Jones et al. |
| 6,095,139 A | 8/2000 | Psaros |
| 6,095,140 A | 8/2000 | Poon et al. |
| 6,102,038 A | 8/2000 | DeVries |
| 6,105,575 A | 8/2000 | Estes et al. |
| 6,116,240 A | 9/2000 | Merrick et al. |
| 6,116,242 A | 9/2000 | Frye et al. |
| 6,116,464 A | 9/2000 | Sanders |
| 6,119,686 A | 9/2000 | Somerson et al. |
| 6,123,073 A | 9/2000 | Schlawin et al. |
| 6,123,074 A | 9/2000 | Hete et al. |
| 6,131,571 A | 10/2000 | Lampotang et al. |
| 6,135,106 A | 10/2000 | Dirks et al. |
| 6,135,967 A | 10/2000 | Fiorenza et al. |
| 6,138,675 A | 10/2000 | Berthon-Jones |
| 6,142,150 A | 11/2000 | O'Mahoney |
| 6,148,814 A | 11/2000 | Clemmer et al. |
| 6,152,129 A | 11/2000 | Berthon-Jones |
| 6,152,132 A | 11/2000 | Psaros |
| 6,152,135 A | 11/2000 | DeVries et al. |
| 6,158,432 A | 12/2000 | Biondi et al. |
| 6,158,433 A | 12/2000 | Ong et al. |
| 6,161,539 A | 12/2000 | Winter |
| 6,176,234 B1 | 1/2001 | Salter et al. |
| 6,192,885 B1 | 2/2001 | Jalde |
| 6,200,271 B1 | 3/2001 | Kuck et al. |
| 6,210,342 B1 | 4/2001 | Kuck et al. |
| 6,213,119 B1 | 4/2001 | Brydon et al. |
| 6,217,524 B1 | 4/2001 | Orr et al. |
| 6,220,244 B1 | 4/2001 | McLaughlin |
| 6,220,245 B1 | 4/2001 | Takabayashi et al. |
| 6,230,708 B1 | 5/2001 | Radko |
| 6,238,351 B1 | 5/2001 | Orr et al. |
| 6,241,681 B1 | 6/2001 | Haryadi et al. |
| 6,253,765 B1 | 7/2001 | Hognelid et al. |
| 6,258,038 B1 | 7/2001 | Haryadi et al. |
| 6,269,812 B1 | 8/2001 | Wallace et al. |
| 6,273,444 B1 | 8/2001 | Power |
| 6,279,569 B1 | 8/2001 | Berthon-Jones |
| 6,283,119 B1 | 9/2001 | Bourdon |
| 6,286,508 B1 | 9/2001 | Remmers et al. |
| 6,287,264 B1 | 9/2001 | Hoffman |
| 6,295,330 B1 | 9/2001 | Skog et al. |
| 6,295,985 B1 | 10/2001 | Kock et al. |
| 6,305,372 B1 | 10/2001 | Servidio |
| 6,305,373 B1 | 10/2001 | Wallace et al. |
| 6,305,374 B1 | 10/2001 | Zdrojkowski et al. |
| 6,306,098 B1 | 10/2001 | Orr et al. |
| 6,308,706 B1 | 10/2001 | Lammers et al. |
| 6,309,360 B1 | 10/2001 | Mault |
| 6,318,365 B1 | 11/2001 | Vogele et al. |
| 6,321,748 B1 | 11/2001 | O'Mahoney |
| 6,325,785 B1 | 12/2001 | Babkes et al. |
| 6,345,619 B1 | 2/2002 | Finn |
| 6,349,922 B1 | 2/2002 | Rydin |
| 6,357,438 B1 | 3/2002 | Hansen |
| 6,360,741 B2 | 3/2002 | Truschel |
| 6,360,745 B1 | 3/2002 | Wallace et al. |
| 6,369,838 B1 | 4/2002 | Wallace et al. |
| 6,371,113 B1 | 4/2002 | Tobia et al. |
| 6,412,483 B1 | 7/2002 | Jones et al. |
| 6,415,788 B1 | 7/2002 | Clawson et al. |
| 6,419,634 B1 | 7/2002 | Gaston, IV et al. |
| 6,425,395 B1 | 7/2002 | Brewer et al. |
| 6,427,689 B1 | 8/2002 | Estes et al. |
| 6,427,692 B1 | 8/2002 | Hoglund |
| 6,439,229 B1 | 8/2002 | Du et al. |
| 6,443,154 B1 | 9/2002 | Jalde et al. |
| 6,450,163 B1 | 9/2002 | Blacker et al. |
| 6,450,968 B1 | 9/2002 | Wallen et al. |
| 6,457,472 B1 | 10/2002 | Schwartz et al. |
| 6,467,477 B1 | 10/2002 | Frank et al. |
| 6,467,478 B1 | 10/2002 | Merrick et al. |
| 6,484,719 B1 | 11/2002 | Berthon-Jones |
| 6,510,846 B1 | 1/2003 | O'Rourke |
| 6,512,938 B2 | 1/2003 | Claure et al. |
| 6,523,537 B1 | 2/2003 | Mas Marfany |
| 6,523,538 B1 | 2/2003 | Wikefeldt |
| 6,526,970 B2 | 3/2003 | DeVries et al. |
| 6,532,957 B2 | 3/2003 | Berthon-Jones |
| 6,532,960 B1 | 3/2003 | Yurko |
| 6,536,432 B2 | 3/2003 | Truschel |
| 6,537,228 B1 | 3/2003 | Lambert |
| 6,539,940 B2 | 4/2003 | Zdrojkowski et al. |
| 6,543,449 B1 | 4/2003 | Woodring et al. |
| 6,546,930 B1 | 4/2003 | Emerson et al. |
| 6,550,478 B2 | 4/2003 | Remmers et al. |
| 6,550,479 B1 | 4/2003 | Duxbury |
| 6,553,991 B1 | 4/2003 | Isaza |
| 6,553,992 B1 | 4/2003 | Berthon-Jones et al. |
| 6,557,553 B1 | 5/2003 | Borrello |
| 6,557,554 B1 | 5/2003 | Sugiura |
| 6,564,798 B1 | 5/2003 | Jalde |
| 6,568,387 B2 | 5/2003 | Davenport et al. |
| 6,571,795 B2 | 6/2003 | Bourdon |
| 6,572,561 B2 | 6/2003 | Mault |
| 6,575,163 B1 | 6/2003 | Berthon-Jones |
| 6,575,164 B1 | 6/2003 | Jaffe et al. |
| 6,575,165 B1 | 6/2003 | Cook et al. |
| 6,575,918 B2 | 6/2003 | Kline |
| 6,578,575 B1 | 6/2003 | Jonson |
| 6,584,973 B1 | 7/2003 | Biondi et al. |
| 6,588,422 B1 | 7/2003 | Berthon-Jones et al. |
| 6,588,423 B1 | 7/2003 | Sinderby |
| 6,595,212 B1 | 7/2003 | Arnott |
| 6,601,583 B2 | 8/2003 | Pessala et al. |
| 6,606,994 B1 | 8/2003 | Clark |
| 6,609,517 B1 | 8/2003 | Estes et al. |
| 6,615,834 B2 | 9/2003 | Gradon et al. |
| 6,616,615 B2 | 9/2003 | Mault |
| 6,619,289 B1 | 9/2003 | Mashak |
| 6,622,725 B1 | 9/2003 | Fisher et al. |
| 6,622,726 B1 | 9/2003 | Du |
| 6,626,175 B2 | 9/2003 | Jafari et al. |
| 6,629,527 B1 | 10/2003 | Estes et al. |
| 6,629,934 B2 | 10/2003 | Mault et al. |
| 6,631,716 B1 | 10/2003 | Robinson et al. |
| 6,640,806 B2 | 11/2003 | Yurko |
| 6,644,310 B1 | 11/2003 | Delache et al. |
| 6,659,100 B2 | 12/2003 | O'Rourke |
| 6,659,101 B2 | 12/2003 | Berthon-Jones |
| 6,662,032 B1 | 12/2003 | Gavish et al. |
| 6,668,824 B1 | 12/2003 | Isaza et al. |
| 6,671,529 B2 | 12/2003 | Claure et al. |
| 6,675,801 B2 | 1/2004 | Wallace et al. |
| 6,679,258 B1 | 1/2004 | Strom |
| 6,688,307 B2 | 2/2004 | Berthon-Jones |
| 6,694,978 B1 | 2/2004 | Bennarsten |
| 6,701,926 B2 | 3/2004 | Olsen et al. |
| 6,705,314 B1 | 3/2004 | O'Dea |
| 6,718,974 B1 | 4/2004 | Moberg |
| 6,722,359 B2 | 4/2004 | Chalvignac |

(56) References Cited

U.S. PATENT DOCUMENTS

| | | |
|---|---|---|
| 6,722,360 B2 | 4/2004 | Doshi |
| 6,722,365 B2 | 4/2004 | Nilsson et al. |
| 6,723,055 B2 | 4/2004 | Hoffman |
| 6,723,132 B2 | 4/2004 | Salehpoor |
| 6,725,447 B1 | 4/2004 | Gilman et al. |
| 6,729,331 B2 | 5/2004 | Kay |
| 6,739,334 B2 | 5/2004 | Valeij |
| 6,739,337 B2 | 5/2004 | Isaza |
| 6,752,150 B1 | 6/2004 | Remmers et al. |
| 6,752,151 B2 | 6/2004 | Hill |
| 6,755,193 B2 | 6/2004 | Berthon-Jones et al. |
| 6,758,216 B1 | 7/2004 | Berthon-Jones et al. |
| 6,761,167 B1 | 7/2004 | Nadjafizadeh et al. |
| 6,761,168 B1 | 7/2004 | Nadjafizadeh et al. |
| 6,763,829 B2 | 7/2004 | Jaffe et al. |
| 6,772,762 B2 | 8/2004 | Piesinger |
| 6,776,159 B2 | 8/2004 | Pelerossi et al. |
| 6,786,216 B2 | 9/2004 | O'Rourke |
| 6,789,541 B2 | 9/2004 | Olsen et al. |
| 6,805,121 B1 | 10/2004 | Flood et al. |
| 6,810,876 B2 | 11/2004 | Berthon-Jones |
| 6,814,074 B1 | 11/2004 | Nadjafizadeh et al. |
| 6,823,866 B2 | 11/2004 | Jafari et al. |
| 6,843,250 B2 | 1/2005 | Efrati |
| 6,854,462 B2 | 2/2005 | Berthon-Jones et al. |
| 6,863,068 B2 | 3/2005 | Jamison et al. |
| 6,863,656 B2 | 3/2005 | Lurie |
| 6,866,040 B1 | 3/2005 | Bourdon |
| 6,874,503 B2 | 4/2005 | Rydgren |
| 6,877,511 B2 | 4/2005 | DeVries et al. |
| 6,886,558 B2 | 5/2005 | Tanaka |
| 6,896,713 B1 | 5/2005 | Eckerbom et al. |
| 6,910,480 B1 | 6/2005 | Berthon-Jones |
| 6,910,481 B2 | 6/2005 | Kimmel et al. |
| 6,915,803 B2 | 7/2005 | Berthon-Jones et al. |
| 6,920,875 B1 | 7/2005 | Hill et al. |
| 6,920,877 B2 | 7/2005 | Remmers et al. |
| 6,920,878 B2 | 7/2005 | Sinderby et al. |
| 6,932,084 B2 | 8/2005 | Estes et al. |
| 6,938,619 B1 | 9/2005 | Hickle |
| 6,945,248 B2 | 9/2005 | Berthon-Jones |
| 6,948,497 B2 | 9/2005 | Zdrojkowski et al. |
| 6,960,854 B2 | 11/2005 | Nadjafizadeh et al. |
| 6,962,155 B1 | 11/2005 | Sinderby |
| 6,968,840 B2 | 11/2005 | Smith et al. |
| 6,986,347 B2 | 1/2006 | Hickle |
| 6,986,349 B2 | 1/2006 | Lurie |
| 6,988,498 B2 | 1/2006 | Berthon-Jones et al. |
| 6,990,980 B2 | 1/2006 | Richey, II |
| 7,000,612 B2 | 2/2006 | Jafari et al. |
| 7,008,380 B1 | 3/2006 | Rees et al. |
| 7,011,091 B2 | 3/2006 | Hill et al. |
| 7,011,092 B2 | 3/2006 | McCombs et al. |
| 7,013,892 B2 | 3/2006 | Estes et al. |
| 7,017,576 B2 | 3/2006 | Olsen et al. |
| 7,032,589 B2 | 4/2006 | Kerechanin et al. |
| 7,036,504 B2 | 5/2006 | Wallace et al. |
| 7,040,315 B1 | 5/2006 | Strömberg |
| 7,040,320 B2 | 5/2006 | Fjeld et al. |
| 7,040,321 B2 | 5/2006 | Göbel |
| 7,043,979 B2 | 5/2006 | Smith et al. |
| 7,055,522 B2 | 6/2006 | Berthon-Jones |
| 7,066,175 B2 | 6/2006 | Hamilton et al. |
| 7,066,177 B2 | 6/2006 | Pittaway et al. |
| 7,070,570 B2 | 7/2006 | Sanderson et al. |
| 7,073,501 B2 | 7/2006 | Remmers et al. |
| 7,077,131 B2 | 7/2006 | Hansen |
| 7,077,132 B2 | 7/2006 | Berthon-Jones |
| RE39,225 E | 8/2006 | Isaza et al. |
| 7,087,027 B2 | 8/2006 | Page |
| 7,089,932 B2 | 8/2006 | Dodds |
| 7,096,866 B2 | 8/2006 | Be'eri et al. |
| 7,100,607 B2 | 9/2006 | Zdrojkowski et al. |
| 7,100,608 B2 | 9/2006 | Brewer et al. |
| 7,100,609 B2 | 9/2006 | Berthon-Jones et al. |
| 7,104,962 B2 | 9/2006 | Lomask et al. |
| 7,107,991 B2 | 9/2006 | Kolobow |
| 7,117,438 B2 | 10/2006 | Wallace et al. |
| 7,118,537 B2 | 10/2006 | Baddour |
| 7,121,277 B2 | 10/2006 | Ström |
| 7,122,010 B2 | 10/2006 | Böhm et al. |
| 7,128,069 B2 | 10/2006 | Farrugia et al. |
| 7,137,389 B2 | 11/2006 | Berthon-Jones |
| 7,152,598 B2 | 12/2006 | Morris et al. |
| 7,152,604 B2 | 12/2006 | Hickle et al. |
| 7,168,429 B2 | 1/2007 | Matthews et al. |
| 7,168,597 B1 | 1/2007 | Jones et al. |
| 7,195,013 B2 | 3/2007 | Lurie |
| 7,195,028 B2 | 3/2007 | Basset et al. |
| 7,204,251 B2 | 4/2007 | Lurie |
| 7,210,478 B2 | 5/2007 | Banner et al. |
| 7,211,049 B2 | 5/2007 | Bradley et al. |
| 7,222,623 B2 | 5/2007 | DeVries et al. |
| 7,241,269 B2 | 7/2007 | McCawley et al. |
| 7,246,618 B2 | 7/2007 | Habashi |
| 7,267,122 B2 | 9/2007 | Hill |
| 7,267,652 B2 | 9/2007 | Coyle et al. |
| 7,270,126 B2 | 9/2007 | Wallace et al. |
| 7,270,128 B2 | 9/2007 | Berthon-Jones et al. |
| 7,275,540 B2 | 10/2007 | Bolam et al. |
| 7,276,031 B2 | 10/2007 | Norman et al. |
| 7,291,115 B2 | 11/2007 | Cardona Burrul |
| 7,296,573 B2 | 11/2007 | Estes et al. |
| 7,302,949 B2 | 12/2007 | Pelerossi et al. |
| 7,311,668 B2 | 12/2007 | Lurie |
| 7,320,321 B2 | 1/2008 | Pranger et al. |
| 7,347,825 B2 | 3/2008 | Vaughan et al. |
| 7,367,337 B2 | 5/2008 | Berthon-Jones et al. |
| 7,369,757 B2 | 5/2008 | Farbarik |
| 7,370,650 B2 | 5/2008 | Nadjafizadeh et al. |
| 7,390,304 B2 | 6/2008 | Chen et al. |
| 7,392,806 B2 | 7/2008 | Yuen et al. |
| 7,428,902 B2 | 9/2008 | Du et al. |
| 7,460,959 B2 | 12/2008 | Jafari |
| 7,465,275 B2 | 12/2008 | Stenqvist |
| 7,467,012 B1 | 12/2008 | Park et al. |
| 7,472,702 B2 | 1/2009 | Beck et al. |
| 7,475,685 B2 | 1/2009 | Dietz et al. |
| 7,478,634 B2 | 1/2009 | Jam |
| 7,481,222 B2 | 1/2009 | Reissmann |
| 7,484,508 B2 | 2/2009 | Younes |
| 7,487,773 B2 | 2/2009 | Li |
| 7,487,774 B2 | 2/2009 | Acker |
| 7,487,778 B2 | 2/2009 | Freitag |
| 7,500,483 B2 | 3/2009 | Colman et al. |
| 7,509,957 B2 | 3/2009 | Duquette et al. |
| 7,525,663 B2 | 4/2009 | Kwok et al. |
| 7,527,056 B2 | 5/2009 | Turiello |
| 7,533,670 B1 | 5/2009 | Freitag et al. |
| 7,533,671 B2 | 5/2009 | Gonzalez et al. |
| RE40,814 E | 6/2009 | Van Brunt et al. |
| 7,547,285 B2 | 6/2009 | Kline |
| 7,552,731 B2 | 6/2009 | Jorczak et al. |
| 7,556,038 B2 | 7/2009 | Kirby et al. |
| 7,556,041 B2 | 7/2009 | Madsen |
| 7,556,042 B2 | 7/2009 | West et al. |
| 7,562,657 B2 | 7/2009 | Blanch et al. |
| 7,588,033 B2 | 9/2009 | Wondka |
| 7,610,914 B2 | 11/2009 | Bolam et al. |
| 7,617,824 B2 | 11/2009 | Doyle |
| 7,621,269 B2 | 11/2009 | Turiello |
| 7,621,270 B2 | 11/2009 | Morris et al. |
| 7,621,271 B2 | 11/2009 | Brugnoli |
| 7,634,998 B1 | 12/2009 | Fenley |
| 7,644,713 B2 | 1/2010 | Berthon-Jones |
| 7,654,802 B2 | 2/2010 | Crawford, Jr. et al. |
| 7,661,428 B2 | 2/2010 | Berthon-Jones |
| 7,673,629 B2 | 3/2010 | Turiello |
| 7,677,247 B2 | 3/2010 | Turiello |
| 7,682,312 B2 | 3/2010 | Lurie |
| 7,686,019 B2 | 3/2010 | Weiss et al. |
| 7,694,677 B2 | 4/2010 | Tang |
| 7,694,678 B2 | 4/2010 | Turiello |
| 7,699,788 B2 | 4/2010 | Kuck et al. |

(56) References Cited

U.S. PATENT DOCUMENTS

| | | |
|---|---|---|
| 7,708,015 B2 | 5/2010 | Seeger et al. |
| 7,717,112 B2 | 5/2010 | Sun et al. |
| 7,717,113 B2 | 5/2010 | Andrieux |
| 7,717,858 B2 | 5/2010 | Massad |
| 7,721,735 B2 | 5/2010 | Hamilton et al. |
| 7,721,736 B2 | 5/2010 | Urias et al. |
| 7,722,546 B2 | 5/2010 | Madaus et al. |
| D618,356 S | 6/2010 | Ross |
| 7,735,486 B2 | 6/2010 | Payne |
| 7,735,492 B2 | 6/2010 | Doshi et al. |
| 7,740,591 B1 | 6/2010 | Starr et al. |
| 7,753,052 B2 | 7/2010 | Tanaka |
| 7,770,578 B2 | 8/2010 | Estes et al. |
| 7,775,207 B2 | 8/2010 | Jaffe et al. |
| 7,779,840 B2 | 8/2010 | Acker et al. |
| 7,784,461 B2 | 8/2010 | Figueiredo et al. |
| 7,793,656 B2 | 9/2010 | Johnson |
| 7,798,145 B2 | 9/2010 | Weismann et al. |
| 7,798,148 B2 | 9/2010 | Doshi et al. |
| 7,802,571 B2 | 9/2010 | Tehrani |
| 7,806,120 B2 | 10/2010 | Loomas et al. |
| 7,810,496 B2 | 10/2010 | Estes et al. |
| 7,810,497 B2 | 10/2010 | Pittman et al. |
| 7,810,498 B1 | 10/2010 | Patterson |
| 7,814,906 B2 | 10/2010 | Moretti |
| 7,814,908 B2 | 10/2010 | Psaros |
| 7,819,815 B2 | 10/2010 | Younes |
| 7,823,588 B2 | 11/2010 | Hansen |
| 7,827,988 B2 | 11/2010 | Matthews et al. |
| 7,828,741 B2 | 11/2010 | Kline et al. |
| 7,841,347 B2 | 11/2010 | Sonnenschein et al. |
| 7,846,739 B2 | 12/2010 | von Bahr et al. |
| 7,849,854 B2 | 12/2010 | DeVries et al. |
| 7,850,619 B2 | 12/2010 | Gavish et al. |
| 7,855,716 B2 | 12/2010 | McCreary et al. |
| 7,856,979 B2 | 12/2010 | Doshi et al. |
| 7,861,716 B2 | 1/2011 | Borrello |
| 7,866,318 B2 | 1/2011 | Bassin |
| 7,870,857 B2 | 1/2011 | Dhuper et al. |
| D632,796 S | 2/2011 | Ross et al. |
| D632,797 S | 2/2011 | Ross et al. |
| 7,882,835 B2 | 2/2011 | Eger et al. |
| 7,883,471 B2 | 2/2011 | Aljuri et al. |
| 7,885,771 B2 | 2/2011 | Roecker et al. |
| 7,886,739 B2 | 2/2011 | Soliman et al. |
| 7,886,740 B2 | 2/2011 | Thomas et al. |
| 7,891,354 B2 | 2/2011 | Farbarik |
| 7,893,560 B2 | 2/2011 | Carter |
| 7,900,626 B2 | 3/2011 | Daly |
| 7,905,231 B2 | 3/2011 | Chalvignac |
| 7,909,034 B2 | 3/2011 | Sinderby et al. |
| 7,913,690 B2 | 3/2011 | Fisher et al. |
| 7,918,222 B2 | 4/2011 | Chen |
| 7,918,223 B2 | 4/2011 | Soliman et al. |
| 7,920,067 B2 | 4/2011 | Durtschi et al. |
| 7,928,852 B2 | 4/2011 | Durtschi et al. |
| D638,852 S | 5/2011 | Skidmore et al. |
| 7,934,499 B2 | 5/2011 | Berthon-Jones |
| 7,938,114 B2 | 5/2011 | Matthews et al. |
| 7,963,283 B2 | 6/2011 | Sinderby |
| 7,970,475 B2 | 6/2011 | Tehrani et al. |
| 7,971,589 B2 | 7/2011 | Mashak et al. |
| 7,984,712 B2 | 7/2011 | Soliman et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 7,992,564 B2 | 8/2011 | Doshi et al. |
| 7,997,271 B2 | 8/2011 | Hickle et al. |
| 8,001,967 B2 | 8/2011 | Wallace et al. |
| 8,002,154 B2 | 8/2011 | Fontela et al. |
| D645,158 S | 9/2011 | Sanchez et al. |
| 8,011,363 B2 | 9/2011 | Johnson |
| 8,011,364 B2 | 9/2011 | Johnson |
| 8,011,366 B2 | 9/2011 | Knepper |
| 8,015,974 B2 | 9/2011 | Christopher et al. |
| 8,020,558 B2 | 9/2011 | Christopher et al. |
| 8,021,308 B2 | 9/2011 | Carlson et al. |
| 8,021,309 B2 | 9/2011 | Zilberg |
| 8,021,310 B2 | 9/2011 | Sanborn et al. |
| 8,033,280 B2 | 10/2011 | Heinonen |
| D649,157 S | 11/2011 | Skidmore et al. |
| 8,051,853 B2 | 11/2011 | Berthon-Jones |
| 8,070,709 B2 | 12/2011 | Childers |
| 8,083,677 B2 | 12/2011 | Rohde |
| D652,521 S | 1/2012 | Ross et al. |
| D652,936 S | 1/2012 | Ross et al. |
| 8,105,310 B2 | 1/2012 | Klein |
| D653,749 S | 2/2012 | Winter et al. |
| 8,113,062 B2 | 2/2012 | Graboi et al. |
| 8,122,885 B2 | 2/2012 | Berthon-Jones et al. |
| D655,405 S | 3/2012 | Winter et al. |
| D655,809 S | 3/2012 | Winter et al. |
| D656,237 S | 3/2012 | Sanchez et al. |
| 8,136,521 B2 | 3/2012 | Matthews et al. |
| 8,152,116 B2 | 4/2012 | Westberg |
| RE43,398 E | 5/2012 | Honkonen et al. |
| 8,181,643 B2 | 5/2012 | Friedberg |
| 8,181,648 B2 | 5/2012 | Perine et al. |
| 8,181,649 B2 | 5/2012 | Brunner |
| 8,187,184 B2 | 5/2012 | Muller et al. |
| 8,210,173 B2 | 7/2012 | Vandine |
| 8,210,174 B2 | 7/2012 | Farbarik |
| 8,211,128 B1 | 7/2012 | Facundus et al. |
| 8,216,159 B1 | 7/2012 | Leiboff |
| 8,217,218 B2 | 7/2012 | Court et al. |
| 8,225,796 B2 | 7/2012 | Davenport et al. |
| 8,235,930 B1 | 8/2012 | McCall |
| 8,240,684 B2 | 8/2012 | Ross et al. |
| 8,251,923 B2 | 8/2012 | Carrez et al. |
| 8,256,418 B2 | 9/2012 | Bassin |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,288,607 B2 | 10/2012 | Court et al. |
| 8,302,600 B2 | 11/2012 | Andrieux et al. |
| 8,302,602 B2 | 11/2012 | Andrieux et al. |
| 8,333,191 B2 | 12/2012 | Heinonen |
| 8,418,691 B2 | 4/2013 | Jafari et al. |
| 8,424,521 B2 | 4/2013 | Jafari et al. |
| 8,457,706 B2 | 6/2013 | Baker, Jr. |
| 8,459,260 B2 | 6/2013 | Bassin |
| 8,544,466 B2 | 10/2013 | Blanch |
| 8,733,351 B2 | 5/2014 | Berthon-Jones |
| 8,746,248 B2 | 6/2014 | Jafari et al. |
| 8,789,526 B2 | 7/2014 | Kwok |
| 8,792,949 B2 | 7/2014 | Baker, Jr. |
| 8,910,633 B2 | 12/2014 | Younes |
| 9,364,624 B2 | 6/2016 | Jafari |
| 9,468,398 B2 | 10/2016 | Blanch |
| 9,498,589 B2 | 11/2016 | Jafari et al. |
| 9,629,970 B2 | 4/2017 | Matthews |
| 10,328,219 B2 | 6/2019 | Rao |
| 10,342,941 B2 | 7/2019 | Kwok |
| 10,350,379 B2 | 7/2019 | Sweeney |
| 10,709,854 B2 | 7/2020 | Jafari |
| 2002/0017301 A1 | 2/2002 | Lundin |
| 2002/0023645 A1* | 2/2002 | Zdrojkowski ....... A61M 16/026 128/204.23 |
| 2002/0026941 A1 | 3/2002 | Biondi et al. |
| 2002/0042564 A1 | 4/2002 | Cooper et al. |
| 2002/0042565 A1 | 4/2002 | Cooper et al. |
| 2002/0117173 A1 | 8/2002 | Lynn et al. |
| 2002/0138213 A1 | 9/2002 | Mault |
| 2002/0144681 A1 | 10/2002 | Cewers et al. |
| 2003/0029453 A1 | 2/2003 | Smith et al. |
| 2003/0062045 A1 | 4/2003 | Woodring et al. |
| 2003/0140925 A1 | 7/2003 | Sapienza et al. |
| 2003/0225339 A1 | 12/2003 | Orr et al. |
| 2004/0089561 A1 | 5/2004 | Herman |
| 2004/0138577 A1 | 7/2004 | Kline |
| 2004/0149282 A1 | 8/2004 | Hickle |
| 2004/0163648 A1 | 8/2004 | Burton |
| 2004/0244804 A1 | 12/2004 | Olsen et al. |

(56) References Cited

U.S. PATENT DOCUMENTS

| | | | |
|---|---|---|---|
| 2004/0255943 A1* | 12/2004 | Morris | A61M 16/024 128/204.23 |
| 2004/0261793 A1 | 12/2004 | Stromberg et al. | |
| 2005/0034724 A1 | 2/2005 | O'Dea | |
| 2005/0039748 A1 | 2/2005 | Andrieux | |
| 2005/0085865 A1 | 4/2005 | Tehrani | |
| 2005/0085867 A1 | 4/2005 | Tehrani et al. | |
| 2005/0085868 A1 | 4/2005 | Tehrani et al. | |
| 2005/0098177 A1 | 5/2005 | Haj-Yahya et al. | |
| 2005/0139211 A1 | 6/2005 | Alston et al. | |
| 2005/0139212 A1 | 6/2005 | Bourdon | |
| 2005/0150494 A1 | 7/2005 | DeVries et al. | |
| 2005/0166928 A1 | 8/2005 | Jiang | |
| 2005/0217671 A1 | 10/2005 | Fisher et al. | |
| 2005/0279358 A1 | 12/2005 | Richey, II | |
| 2006/0011200 A1 | 1/2006 | Remmers et al. | |
| 2006/0021618 A1 | 2/2006 | Berthon-Jones et al. | |
| 2006/0032499 A1 | 2/2006 | Halsnes | |
| 2006/0122662 A1 | 6/2006 | Tehrani et al. | |
| 2006/0129054 A1 | 6/2006 | Orr et al. | |
| 2006/0130839 A1 | 6/2006 | Bassovitch | |
| 2006/0142815 A1 | 6/2006 | Tehrani et al. | |
| 2006/0174883 A1 | 8/2006 | Aylsworth et al. | |
| 2006/0196507 A1 | 9/2006 | Bradley | |
| 2006/0196508 A1 | 9/2006 | Chalvignac | |
| 2006/0201505 A1 | 9/2006 | Remmers et al. | |
| 2006/0201507 A1 | 9/2006 | Breen | |
| 2006/0217633 A1 | 9/2006 | Glocker et al. | |
| 2006/0241708 A1 | 10/2006 | Boute | |
| 2006/0247508 A1 | 11/2006 | Fennell | |
| 2006/0249148 A1 | 11/2006 | Younes | |
| 2006/0249153 A1 | 11/2006 | DeVries et al. | |
| 2006/0254588 A1 | 11/2006 | Brewer et al. | |
| 2006/0272637 A1 | 12/2006 | Johnson | |
| 2006/0278218 A1 | 12/2006 | Hoffman | |
| 2006/0283451 A1 | 12/2006 | Albertelli | |
| 2007/0000494 A1 | 1/2007 | Banner et al. | |
| 2007/0017515 A1 | 1/2007 | Wallace et al. | |
| 2007/0017518 A1 | 1/2007 | Farrugia et al. | |
| 2007/0017522 A1 | 1/2007 | Be-Eri et al. | |
| 2007/0017523 A1 | 1/2007 | Be-Eri et al. | |
| 2007/0028921 A1 | 2/2007 | Banner et al. | |
| 2007/0044796 A1 | 3/2007 | Zdrojkowski et al. | |
| 2007/0062531 A1 | 3/2007 | Fisher et al. | |
| 2007/0062532 A1 | 3/2007 | Choncholas | |
| 2007/0062533 A1 | 3/2007 | Choncholas et al. | |
| 2007/0068528 A1 | 3/2007 | Bohm et al. | |
| 2007/0068530 A1 | 3/2007 | Pacey | |
| 2007/0073183 A1 | 3/2007 | Kline | |
| 2007/0077200 A1 | 4/2007 | Baker | |
| 2007/0089741 A1 | 4/2007 | Bohm et al. | |
| 2007/0095347 A1 | 5/2007 | Lampotang et al. | |
| 2007/0101992 A1* | 5/2007 | Soliman | A61M 16/026 128/204.21 |
| 2007/0113854 A1 | 5/2007 | Mcauliffe | |
| 2007/0123792 A1 | 5/2007 | Kline | |
| 2007/0125377 A1 | 6/2007 | Heinonen et al. | |
| 2007/0129646 A1 | 6/2007 | Heinonen et al. | |
| 2007/0135736 A1 | 6/2007 | Addington et al. | |
| 2007/0144521 A1 | 6/2007 | DeVries et al. | |
| 2007/0144523 A1 | 6/2007 | Bolam et al. | |
| 2007/0157930 A1 | 7/2007 | Soliman et al. | |
| 2007/0157931 A1 | 7/2007 | Parker et al. | |
| 2007/0163579 A1 | 7/2007 | Li et al. | |
| 2007/0181122 A1 | 8/2007 | Mulier | |
| 2007/0227537 A1 | 10/2007 | Bemister et al. | |
| 2007/0232952 A1 | 10/2007 | Baddour | |
| 2007/0251532 A1 | 11/2007 | Friedberg | |
| 2007/0255160 A1 | 11/2007 | Daly | |
| 2007/0272241 A1 | 11/2007 | Sanborn et al. | |
| 2007/0283958 A1 | 12/2007 | Naghavi | |
| 2007/0284361 A1 | 12/2007 | Nadjafizadeh et al. | |
| 2008/0000475 A1 | 1/2008 | Hill | |
| 2008/0000478 A1 | 1/2008 | Matthiessen et al. | |
| 2008/0033304 A1 | 2/2008 | Dalal et al. | |
| 2008/0041382 A1 | 2/2008 | Matthews et al. | |
| 2008/0041383 A1 | 2/2008 | Matthews et al. | |
| 2008/0045825 A1 | 2/2008 | Melker et al. | |
| 2008/0045845 A1 | 2/2008 | Pfeiffer et al. | |
| 2008/0051674 A1 | 2/2008 | Davenport et al. | |
| 2008/0053438 A1 | 3/2008 | DeVries et al. | |
| 2008/0053441 A1 | 3/2008 | Gottlib et al. | |
| 2008/0053443 A1 | 3/2008 | Estes et al. | |
| 2008/0053444 A1 | 3/2008 | Estes et al. | |
| 2008/0060646 A1 | 3/2008 | Isaza | |
| 2008/0060656 A1 | 3/2008 | Isaza | |
| 2008/0066753 A1 | 3/2008 | Martin et al. | |
| 2008/0072896 A1 | 3/2008 | Setzer et al. | |
| 2008/0072901 A1 | 3/2008 | Habashi | |
| 2008/0072902 A1 | 3/2008 | Setzer et al. | |
| 2008/0072904 A1 | 3/2008 | Becker et al. | |
| 2008/0078390 A1 | 4/2008 | Milne et al. | |
| 2008/0078395 A1 | 4/2008 | Ho et al. | |
| 2008/0083644 A1 | 4/2008 | Janbakhsh et al. | |
| 2008/0091117 A1 | 4/2008 | Choncholas et al. | |
| 2008/0092894 A1 | 4/2008 | Nicolazzi et al. | |
| 2008/0097234 A1 | 4/2008 | Nicolazzi et al. | |
| 2008/0110461 A1 | 5/2008 | Mulqueeny et al. | |
| 2008/0110462 A1 | 5/2008 | Chekal et al. | |
| 2008/0135044 A1 | 6/2008 | Freitag et al. | |
| 2008/0163872 A1 | 7/2008 | Negele et al. | |
| 2008/0168988 A1 | 7/2008 | Lu | |
| 2008/0168990 A1 | 7/2008 | Cooke et al. | |
| 2008/0178874 A1 | 7/2008 | Doshi et al. | |
| 2008/0183094 A1 | 7/2008 | Schonfuss et al. | |
| 2008/0183239 A1 | 7/2008 | Tehrani et al. | |
| 2008/0183240 A1 | 7/2008 | Tehrani et al. | |
| 2008/0185002 A1 | 8/2008 | Berthon-Jones et al. | |
| 2008/0188903 A1 | 8/2008 | Tehrani et al. | |
| 2008/0196720 A1 | 8/2008 | Kollmeyer et al. | |
| 2008/0200775 A1 | 8/2008 | Lynn | |
| 2008/0202517 A1 | 8/2008 | Mitton et al. | |
| 2008/0202518 A1 | 8/2008 | Mitton et al. | |
| 2008/0202525 A1 | 8/2008 | Mitton et al. | |
| 2008/0202528 A1 | 8/2008 | Carter et al. | |
| 2008/0208281 A1 | 8/2008 | Tehrani et al. | |
| 2008/0214947 A1 | 9/2008 | Hunt et al. | |
| 2008/0221469 A1 | 9/2008 | Shevchuk | |
| 2008/0221470 A1 | 9/2008 | Sather et al. | |
| 2008/0223361 A1 | 9/2008 | Nieuwstad | |
| 2008/0230061 A1 | 9/2008 | Tham | |
| 2008/0230062 A1 | 9/2008 | Tham | |
| 2008/0236582 A1 | 10/2008 | Tehrani | |
| 2008/0257349 A1 | 10/2008 | Hedner et al. | |
| 2008/0276939 A1 | 11/2008 | Tiedje | |
| 2008/0283060 A1 | 11/2008 | Bassin | |
| 2008/0295837 A1 | 12/2008 | McCormick et al. | |
| 2008/0302359 A1 | 12/2008 | Loomas et al. | |
| 2008/0314385 A1 | 12/2008 | Brunner et al. | |
| 2009/0000621 A1 | 1/2009 | Haggblom et al. | |
| 2009/0007914 A1 | 1/2009 | Bateman | |
| 2009/0013999 A1 | 1/2009 | Bassin | |
| 2009/0014007 A1 | 1/2009 | Brambilla et al. | |
| 2009/0020119 A1 | 1/2009 | Eger et al. | |
| 2009/0038617 A1 | 2/2009 | Berthon-Jones et al. | |
| 2009/0050153 A1 | 2/2009 | Brunner | |
| 2009/0056708 A1 | 3/2009 | Stenzler et al. | |
| 2009/0056719 A1 | 3/2009 | Newman, Jr. | |
| 2009/0071478 A1 | 3/2009 | Kalfon | |
| 2009/0078251 A1 | 3/2009 | Zucchi et al. | |
| 2009/0082653 A1 | 3/2009 | Rohde | |
| 2009/0084381 A1 | 4/2009 | DeVries et al. | |
| 2009/0088613 A1 | 4/2009 | Marttila et al. | |
| 2009/0090359 A1 | 4/2009 | Daviet et al. | |
| 2009/0093697 A1 | 4/2009 | Mir et al. | |
| 2009/0095297 A1 | 4/2009 | Hallett | |
| 2009/0114223 A1 | 5/2009 | Bonassa | |
| 2009/0133695 A1 | 5/2009 | Rao et al. | |
| 2009/0137919 A1 | 5/2009 | Bar-Lavie et al. | |
| 2009/0137927 A1 | 5/2009 | Miller | |
| 2009/0139522 A1 | 6/2009 | Thomson et al. | |
| 2009/0145441 A1 | 6/2009 | Doshi et al. | |
| 2009/0149730 A1 | 6/2009 | McCrary | |
| 2009/0159082 A1 | 6/2009 | Eger | |

(56) References Cited

U.S. PATENT DOCUMENTS

| | | |
|---|---|---|
| 2009/0165795 A1 | 7/2009 | Nadjafizadeh et al. |
| 2009/0165798 A1 | 7/2009 | Cong et al. |
| 2009/0171176 A1 | 7/2009 | Andersohn |
| 2009/0178675 A1 | 7/2009 | Turiello |
| 2009/0178676 A1 | 7/2009 | Villax et al. |
| 2009/0188502 A1 | 7/2009 | Tiedje |
| 2009/0194100 A1 | 8/2009 | Minagi |
| 2009/0194109 A1 | 8/2009 | Doshi et al. |
| 2009/0205660 A1 | 8/2009 | Thomson et al. |
| 2009/0205661 A1 | 8/2009 | Stephenson et al. |
| 2009/0205663 A1 | 8/2009 | Vandine et al. |
| 2009/0217923 A1 | 9/2009 | Boehm et al. |
| 2009/0221926 A1 | 9/2009 | Younes |
| 2009/0229605 A1 | 9/2009 | Efrati et al. |
| 2009/0229612 A1 | 9/2009 | Levi et al. |
| 2009/0235935 A1 | 9/2009 | Pacey |
| 2009/0241948 A1 | 10/2009 | Clancy et al. |
| 2009/0241951 A1 | 10/2009 | Jafari et al. |
| 2009/0241952 A1 | 10/2009 | Nicolazzi et al. |
| 2009/0241953 A1 | 10/2009 | Vandine et al. |
| 2009/0241955 A1 | 10/2009 | Jafari et al. |
| 2009/0241956 A1 | 10/2009 | Baker, Jr. et al. |
| 2009/0241957 A1 | 10/2009 | Baker, Jr. et al. |
| 2009/0241958 A1 | 10/2009 | Baker, Jr. |
| 2009/0241962 A1 | 10/2009 | Jafari et al. |
| 2009/0241964 A1 | 10/2009 | Aljuri et al. |
| 2009/0247849 A1 | 10/2009 | McCutcheon et al. |
| 2009/0247853 A1 | 10/2009 | Debreczeny |
| 2009/0247891 A1 | 10/2009 | Wood |
| 2009/0250054 A1 | 10/2009 | Loncar et al. |
| 2009/0250059 A1 | 10/2009 | Allum et al. |
| 2009/0250061 A1 | 10/2009 | Marasigan |
| 2009/0255533 A1 | 10/2009 | Freitag et al. |
| 2009/0260625 A1 | 10/2009 | Wondka |
| 2009/0263279 A1 | 10/2009 | Kline et al. |
| 2009/0266360 A1 | 10/2009 | Acker et al. |
| 2009/0270752 A1 | 10/2009 | Coifman |
| 2009/0272381 A1 | 11/2009 | Dellaca et al. |
| 2009/0277448 A1 | 11/2009 | Ahlmen et al. |
| 2009/0281481 A1 | 11/2009 | Harding |
| 2009/0293872 A1 | 12/2009 | Bocke |
| 2009/0293877 A1 | 12/2009 | Blanch et al. |
| 2009/0299430 A1 | 12/2009 | Davies et al. |
| 2009/0301486 A1 | 12/2009 | Masic |
| 2009/0301487 A1 | 12/2009 | Masic |
| 2009/0301488 A1 | 12/2009 | Sun |
| 2009/0301490 A1 | 12/2009 | Masic |
| 2009/0301491 A1 | 12/2009 | Masic et al. |
| 2009/0301492 A1 | 12/2009 | Wysocki et al. |
| 2009/0308393 A1 | 12/2009 | Luceros |
| 2009/0308398 A1 | 12/2009 | Ferdinand et al. |
| 2009/0314294 A1 | 12/2009 | Chalvignac |
| 2009/0314297 A1 | 12/2009 | Mathews |
| 2009/0318851 A1 | 12/2009 | Schenck |
| 2010/0011307 A1 | 1/2010 | Desfossez et al. |
| 2010/0012126 A1 | 1/2010 | Gandini |
| 2010/0018529 A1 | 1/2010 | Chalvignac |
| 2010/0024819 A1 | 2/2010 | Tiedje |
| 2010/0024820 A1 | 2/2010 | Bourdon |
| 2010/0031961 A1 | 2/2010 | Schmidt |
| 2010/0051026 A1 | 3/2010 | Graboi |
| 2010/0051029 A1 | 3/2010 | Jafari et al. |
| 2010/0059058 A1 | 3/2010 | Kuo |
| 2010/0065057 A1 | 3/2010 | Berthon-Jones |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0076322 A1 | 3/2010 | Shrivastav et al. |
| 2010/0076323 A1 | 3/2010 | Shrivastav et al. |
| 2010/0078017 A1 | 4/2010 | Andrieux et al. |
| 2010/0078018 A1 | 4/2010 | Heinonen et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0081958 A1 | 4/2010 | She |
| 2010/0089396 A1 | 4/2010 | Richard et al. |
| 2010/0099999 A1 | 4/2010 | Hemnes et al. |
| 2010/0101574 A1 | 4/2010 | Bassin |
| 2010/0101575 A1 | 4/2010 | Fedorko et al. |
| 2010/0101576 A1 | 4/2010 | Berthon-Jones |
| 2010/0101577 A1 | 4/2010 | Kaestle et al. |
| 2010/0106037 A1 | 4/2010 | Kacmarek et al. |
| 2010/0108066 A1* | 5/2010 | Martin ............... A61M 16/204 128/204.23 |
| 2010/0116270 A1 | 5/2010 | Edwards et al. |
| 2010/0116276 A1 | 5/2010 | Bayasi |
| 2010/0125227 A1 | 5/2010 | Bird |
| 2010/0137733 A1 | 6/2010 | Wang et al. |
| 2010/0137737 A1 | 6/2010 | Addington et al. |
| 2010/0139660 A1 | 6/2010 | Adahan |
| 2010/0147302 A1 | 6/2010 | Selvarajan et al. |
| 2010/0147303 A1 | 6/2010 | Jafari et al. |
| 2010/0170512 A1 | 7/2010 | Kuypers et al. |
| 2010/0175695 A1 | 7/2010 | Jamison |
| 2010/0179392 A1 | 7/2010 | Chang et al. |
| 2010/0180897 A1 | 7/2010 | Malgouyres |
| 2010/0185112 A1 | 7/2010 | Van Kesteren et al. |
| 2010/0186741 A1 | 7/2010 | Aylsworth et al. |
| 2010/0186744 A1 | 7/2010 | Andrieux |
| 2010/0198095 A1 | 8/2010 | Isler |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0222692 A1 | 9/2010 | McCawley et al. |
| 2010/0234758 A1 | 9/2010 | de Menezes |
| 2010/0236553 A1 | 9/2010 | Jafari et al. |
| 2010/0236555 A1 | 9/2010 | Jafari et al. |
| 2010/0241019 A1 | 9/2010 | Varga et al. |
| 2010/0241159 A1 | 9/2010 | Li |
| 2010/0242961 A1 | 9/2010 | Mougel et al. |
| 2010/0249549 A1 | 9/2010 | Baker, Jr. et al. |
| 2010/0249584 A1 | 9/2010 | Albertelli |
| 2010/0252042 A1 | 10/2010 | Kapust et al. |
| 2010/0252046 A1 | 10/2010 | Dahlström et al. |
| 2010/0252048 A1 | 10/2010 | Young et al. |
| 2010/0258123 A1 | 10/2010 | Somaiya et al. |
| 2010/0258124 A1 | 10/2010 | Madaus et al. |
| 2010/0262038 A1 | 10/2010 | Tan et al. |
| 2010/0268106 A1 | 10/2010 | Johnson et al. |
| 2010/0268131 A1 | 10/2010 | Efthimiou |
| 2010/0269834 A1 | 10/2010 | Freitag et al. |
| 2010/0275920 A1 | 11/2010 | Tham et al. |
| 2010/0275921 A1 | 11/2010 | Schindhelm et al. |
| 2010/0282258 A1 | 11/2010 | Tailor et al. |
| 2010/0282259 A1 | 11/2010 | Figueiredo et al. |
| 2010/0286544 A1 | 11/2010 | Tanaka et al. |
| 2010/0288283 A1 | 11/2010 | Campbell et al. |
| 2010/0292601 A1 | 11/2010 | Dompeling et al. |
| 2010/0300445 A1 | 12/2010 | Chatburn et al. |
| 2010/0300446 A1 | 12/2010 | Nicolazzi et al. |
| 2010/0319691 A1 | 12/2010 | Lurie et al. |
| 2010/0324437 A1 | 12/2010 | Freeman et al. |
| 2010/0324439 A1 | 12/2010 | Davenport |
| 2010/0326447 A1 | 12/2010 | Loomas et al. |
| 2010/0331768 A1 | 12/2010 | Hedmann et al. |
| 2010/0331877 A1 | 12/2010 | Li et al. |
| 2011/0000489 A1 | 1/2011 | Laksov |
| 2011/0004108 A1 | 1/2011 | Peyton |
| 2011/0005530 A1 | 1/2011 | Doshi et al. |
| 2011/0009762 A1 | 1/2011 | Eichler et al. |
| 2011/0011400 A1 | 1/2011 | Gentner et al. |
| 2011/0017214 A1 | 1/2011 | Tehrani |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0030686 A1 | 2/2011 | Wilkinson et al. |
| 2011/0034863 A1 | 2/2011 | Hoffa |
| 2011/0036352 A1 | 2/2011 | Estes et al. |
| 2011/0041849 A1 | 2/2011 | Chen et al. |

(56) References Cited

U.S. PATENT DOCUMENTS

| | | |
|---|---|---|
| 2011/0041850 A1 | 2/2011 | Vandine et al. |
| 2011/0061648 A1 | 3/2011 | Durtschi et al. |
| 2011/0061650 A1 | 3/2011 | Heesch |
| 2011/0066060 A1 | 3/2011 | Von Bahr et al. |
| 2011/0071367 A1 | 3/2011 | Court et al. |
| 2011/0073112 A1 | 3/2011 | DiBlasi et al. |
| 2011/0077549 A1 | 3/2011 | Kitai et al. |
| 2011/0088697 A1 | 4/2011 | DeVries et al. |
| 2011/0092841 A1 | 4/2011 | Bassin |
| 2011/0100365 A1 | 5/2011 | Wedler et al. |
| 2011/0100373 A1 | 5/2011 | Efrati et al. |
| 2011/0108041 A1 | 5/2011 | Sather et al. |
| 2011/0112424 A1 | 5/2011 | Kesselman et al. |
| 2011/0112425 A1 | 5/2011 | Muhlsteff et al. |
| 2011/0125052 A1 | 5/2011 | Davenport et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132363 A1 | 6/2011 | Chalvignac |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0178427 A1 | 7/2011 | Tan et al. |
| 2011/0196251 A1 | 8/2011 | Jourdain et al. |
| 2011/0197884 A1 | 8/2011 | Duff et al. |
| 2011/0197886 A1 | 8/2011 | Guttmann et al. |
| 2011/0197892 A1 | 8/2011 | Koledin |
| 2011/0201956 A1 | 8/2011 | Alferness et al. |
| 2011/0203598 A1 | 8/2011 | Favet et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0220112 A1 | 9/2011 | Connor |
| 2011/0226248 A1 | 9/2011 | Duff et al. |
| 2011/0226250 A1 | 9/2011 | LaBollita et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2011/0284003 A1 | 11/2011 | Douglas et al. |
| 2011/0290246 A1 | 12/2011 | Zachar |
| 2011/0293706 A1 | 12/2011 | Ludwig et al. |
| 2011/0313689 A1 | 12/2011 | Holley et al. |
| 2012/0000466 A1 | 1/2012 | Rapoport |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0006328 A1 | 1/2012 | Berthon-Jones |
| 2012/0022441 A1 | 1/2012 | Kelly et al. |
| 2012/0029317 A1 | 2/2012 | Doyle et al. |
| 2012/0030611 A1 | 2/2012 | Skidmore |
| 2012/0060835 A1 | 3/2012 | Mashak |
| 2012/0060841 A1 | 3/2012 | Crawford, Jr. et al. |
| 2012/0065533 A1 | 3/2012 | Carrillo, Jr. et al. |
| 2012/0071729 A1 | 3/2012 | Doyle et al. |
| 2012/0083729 A1 | 4/2012 | Childers |
| 2012/0090610 A1 | 4/2012 | O'Connor et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0139734 A1 | 6/2012 | Olde et al. |
| 2012/0150057 A1 | 6/2012 | Mantri |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0215081 A1 | 8/2012 | Euliano et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0304995 A1 | 12/2012 | Kauc |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0025596 A1 | 1/2013 | Jafari et al. |
| 2013/0025597 A1 | 1/2013 | Doyle et al. |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0167842 A1 | 7/2013 | Jafari et al. |
| 2013/0167843 A1 | 7/2013 | Kimm et al. |
| 2017/0095627 A1 | 4/2017 | Jafari |

OTHER PUBLICATIONS

7200 Ventilatory System: Addendum/Errata. Nellcor Puritan Bennett, Part No. 4-023576-00, Rev. A, Apr. 1988, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

Puritan Bennett 980 Series Ventilator Operator's Manual, Covidien, Jan. 29, 2014, Part. No. 10077893 A Jan. 2014, 506 pages.

\* cited by examiner

METHODS AND SYSTEMS FOR ADAPTIVE BASE FLOW AND LEAK COMPENSATION

CROSS-REFERENCE TO RELATED APPLICATIONS

This application is a continuation of U.S. patent application Ser. No. 15/358,519, entitled "METHODS AND SYSTEMS FOR ADAPTIVE BASE FLOW AND LEAK COMPENSATION," filed on Nov. 22, 2016, which application is a continuation of U.S. patent application Ser. No. 13/341,957, now U.S. Pat. No. 9,498,589, filed on Dec. 31, 2011, the entire disclosures of which are hereby incorporated herein by reference.

INTRODUCTION

Medical ventilator systems have long been used to provide ventilatory and supplemental oxygen support to patients. These ventilators typically comprise a source of pressurized oxygen which is fluidly connected to the patient through a conduit or tubing. Further, ventilators often measure and calculate various ventilator and/or patient parameters during the ventilation of a patient. For example, patient-ventilator synchrony and spirometry are major features with significant clinical utility. Patient-ventilator synchrony ensures timely and adequate ventilator response to patient's respiratory efforts. Spirometry data provides valuable information for patient evaluation and clinical decision making. Accordingly, synchrony (i.e., appropriate triggering from exhalation into inhalation and cycling from inhalation into exhalation) and accuracy of the spirometry data is an important performance characteristic of ventilators. Leak-compensated ventilation aims to ensure optimum synchrony and spirometry data in the presence of system leak conditions.

METHODS AND SYSTEMS FOR ADAPTIVE BASE FLOW AND LEAK COMPENSATION

This disclosure describes systems and methods for providing adaptive base flow scheduling during ventilation of a patient to optimize patient-machine synchrony and accuracy of estimated exhaled as well as inhaled tidal volumes. Further, this disclosure describes systems and methods for providing adaptive inspiratory trigger threshold scheduling during the adaptive base flow scheduling. Further still, this disclosure describes systems and methods for determining an estimated leak flow and adjusting the adaptive base flow scheduling and the adaptive inspiratory trigger threshold scheduling based on the estimated leak flow. Moreover, this disclosure describes systems and methods for determining a change in the estimated leak flow and adjusting the adaptive base flow scheduling and the adaptive inspiratory trigger threshold scheduling based on the change in the estimated leak flow.

According to embodiments, a method is provided for ventilating a patient with a ventilator. The method comprises delivering a base flow to a patient during exhalation, wherein the base flow includes an estimated leak flow. Moreover, the method comprises determining an initial base flow, determining an initial inspiratory trigger threshold, and delivering the initial base flow during at least a first portion of the exhalation while setting an inspiratory trigger threshold to the initial inspiratory trigger threshold. The method further comprises changing the base flow from the initial base flow toward a desired base flow during at least a second portion of exhalation and decreasing an inspiratory trigger threshold from the initial inspiratory trigger threshold toward a desired inspiratory trigger threshold while performing the step of increasing or decreasing the base flow. Moreover, the method comprises determining a change in the estimated leak flow; and progressively adjusting the base flow in a set time period during the exhalation to compensate for the determined change in the estimated leak flow while adjusting the inspiratory trigger threshold in the set time period.

According to further embodiments, a ventilator system is provided comprising a pressure generating system adapted to generate a flow of breathing gas, a ventilation tubing system including a patient interface for connecting the pressure generating system to a patient, and at least one sensor operatively coupled to at least one of the pressure generating system and the ventilation tubing system. The ventilator system further comprising a leak estimation module, wherein the leak estimation module determines a change in the estimated leak flow in the ventilation tubing system by utilizing output from the at least one sensor. Furthermore, the ventilator system comprising a base flow trajectory module, wherein the base flow trajectory module delivers a base flow including the estimated leak flow during exhalation to the patient, wherein the base flow trajectory module changes the base flow delivered to the patient from an initial base flow toward a desired base flow during at least a portion of the exhalation, and wherein the base flow trajectory module progressively adjusts the base flow during a set time period during the exhalation to compensate for the determined change in the estimated leak flow. The ventilator system also comprising an inspiratory trigger threshold trajectory module, wherein the inspiratory trigger threshold trajectory module sets an inspiratory trigger threshold during exhalation, wherein the inspiratory trigger threshold trajectory module decreases the inspiratory trigger threshold from an initial inspiratory trigger threshold towards a desired inspiratory trigger threshold while the base flow trajectory module changes the base flow delivered to the patient. The ventilator system further comprising a processor in communication with the pressure generating system, the at least one sensor, the leak estimation module, the inspiratory trigger threshold trajectory module, and the base flow trajectory module.

According to further embodiments, a computer-readable medium having computer-executable instructions for performing a method of ventilating a patient with a ventilator is provided. The method comprising delivering a base flow to a patient during exhalation, where in the base flow includes an estimated leak flow. The method further comprising determining an initial base flow, determining an initial inspiratory trigger threshold, and delivering the initial base flow during at least a first portion of the exhalation while setting an inspiratory trigger threshold to the initial inspiratory trigger threshold. The method further comprising changing the base flow from the initial base flow toward a desired base flow during at least a second portion of exhalation and decreasing an inspiratory trigger threshold from the initial inspiratory trigger threshold toward a desired inspiratory trigger threshold while performing the step of increasing or decreasing the base flow. Moreover, the method comprising determining a change in the estimated leak flow and progressively adjusting the base flow in a set time period during the exhalation to compensate for the determined change in the estimated leak flow while adjusting the inspiratory trigger threshold in the set time period.

According to further embodiments, a ventilator system is provided comprising means for delivering a base flow to a patient during exhalation, where in the base flow includes an estimated leak flow. The ventilator system further comprising means for determining an initial base flow and means for determining an initial inspiratory trigger threshold. The ventilator system also comprising means for changing the base flow from an initial base flow toward a desired base flow during at least a portion of exhalation and means for decreasing the inspiratory trigger threshold from the initial inspiratory trigger threshold toward a first trigger threshold value while performing the step of increasing or decreasing the base flow. The ventilator system further comprising means for determining a change in the estimated leak flow and means for progressively adjusting the base flow in a set time period during the exhalation to compensate for the determined change in the estimated leak flow while adjusting the inspiratory trigger threshold for the set time period.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of embodiments of systems and methods described below and are not meant to limit the scope of the invention in any manner, which scope shall be based on the claims appended hereto.

DETAILED DESCRIPTION

Figure 1:
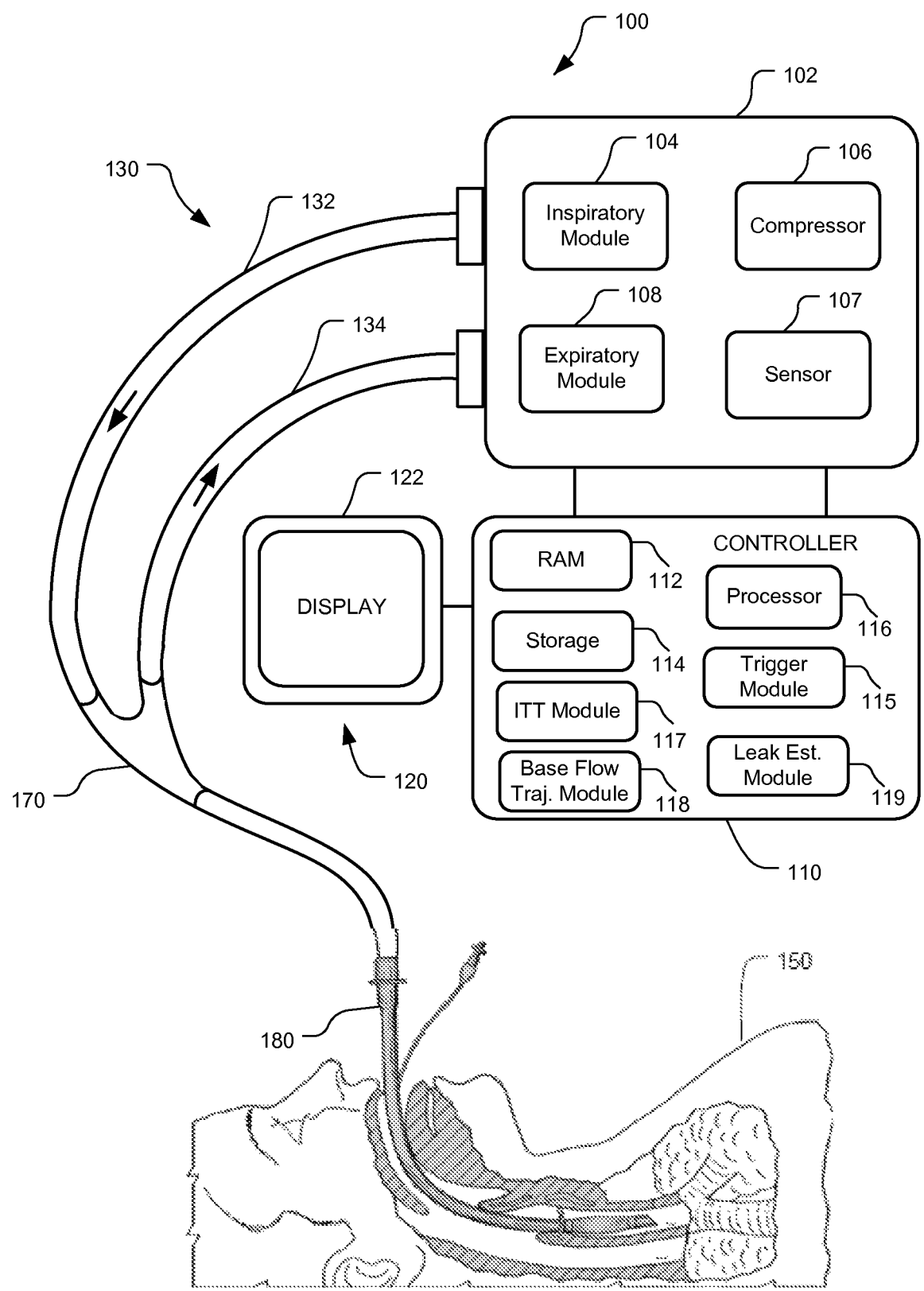
FIG. 1 illustrates an embodiment of a ventilator.

Although the techniques introduced above and discussed in detail below may be implemented for a variety of medical devices, the present disclosure will discuss the implementation of these techniques in the context of a medical ventilator for use in providing ventilation support to a human patient. A person of skill in the art will understand that the technology described in the context of a medical ventilator for human patients could be adapted for use with other systems such as ventilators for non-human patients and general gas transport systems.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves (or regulators) connected to centralized sources of pressurized air and pressurized oxygen. The regulating valves function to regulate flow so that respiratory gas having a desired concentration of oxygen is supplied to the patient at desired pressures and rates. Ventilators capable of operating independently of external sources of pressurized air are also available.

Spirometry data provides valuable information for patient evaluation and clinical decision making. Accordingly, the accuracy of the spirometry data is an important performance characteristic of ventilators. Spirometry volumes may be calculated by integrating the net flow, which is a linear combination of flow rates measured by a number of flow sensors at both the inspiratory (delivery) side and at the exhalation (exhaust) side. These flow sensors possess different uncertainties and the overall accuracy performance is a function of a combination of the properties of individual devices. Exhaled tidal volume is measured during the expiratory phase of a ventilator breath while a base flow is delivered through the patient circuit. To determine the volume of gas inhaled or exhaled by the patient, the net flow (total delivered flow minus total flow through exhalation module) is used for integration. That is, the delivered base flow is subtracted from the sum of the base flow and patient flow exiting through the exhalation port. Delivered flow during exhalation is base flow and consists of a desired combination of appropriate gases. The flow exiting the exhalation module during the active phase of patient exhalation is the sum of base flow delivered by the ventilator and exhaled flow from the patient lung. The flow entering the patient's lung during inhalation is the algebraic sum of the total delivered flow minus the flow compressed in the tubing and any flow exiting through the exhalation module. According to embodiments, for both inhalation spirometry and exhalation spirometry, the flow (volume) lost through tubing leaks should be accounted for accordingly. The spirometry parameter of exhaled tidal volume is measured during patient's active exhalation. Therefore, the smaller the ventilator-delivered base flow is during active exhalation, the smaller the uncertainty contributed by measuring the same quantity by different sensors (once on the delivery side and a second time as a portion of exhaust gas on the exhalation side). This is particularly advantageous under neonatal conditions when tidal volumes and exhaled flow rates are relatively smaller and may be some orders of magnitude smaller than the base flow.

Accordingly, the systems and methods described herein provide ventilation with an adaptive base flow initiation scheduling strategy to optimize the accuracy of estimated exhaled tidal volume. However, changing base flow during exhalation may affect inspiratory triggering and may lead to a false triggering of inspiration prior to a patient desired inspiration. Accordingly, the systems and methods described herein also provide ventilation with an adaptive trigger threshold initiation scheduling strategy to prevent undesired triggering of inspiration. For example, if a change in leak size is detected just prior to or at the beginning of exhalation and a transition of base flow level is to be executed, then, during a first exhalation portion when patient-initiated triggering is unlikely, the inspiratory trigger threshold is set relatively high. However, during a second exhalation period, when patient-initiated triggering is more likely, the inspiratory trigger threshold is reduced. Therefore, as exhalation progresses or during a second portion exhalation, the inspiratory trigger threshold is decreased making it easier for a patient to initiate a desired inspiration. Similarly, if a change in leak size is detected during ongoing exhalation and a base flow transition is executed, then, during a first transitory period the inspiratory trigger threshold is adjusted appropriately to prevent false triggering during the base flow level change and subsequently adjusted towards the desired level in a smooth fashion in coordination with the smooth transition of the base flow level to its final magnitude.

According to embodiments, the adaptive base flow initiation scheduling strategy is further adjusted to account for estimated leak flow from the ventilation tubing circuit. For example, a change in leak flow during exhalation changes the amount of base flow the patient tubing receives, which can provide the system with too much or too little flow during exhalation. When base flow is too high, this may cause patient discomfort; whereas if the base flow is too low, this may cause inaccurate triggering. Accordingly, the adaptive base flow initiation scheduling strategy is adjusted to account for changes in the estimated leak flow detected during exhalation. Such changes in leak size, and consequently in desired base flow, may occur at the beginning of exhalation or at a certain point during the exhalation period. As discussed above, adjustments in base flow during exhalation may affect inspiratory triggering and lead to a false triggering of inspiration prior to a patient desired inspiration. Accordingly, the systems and methods described herein also provide ventilation with an adaptive trigger threshold initiation scheduling strategy that is adjusted during the time period the base flow is adjusted (i.e., according to the adaptive base flow initiation scheduling strategy) to account for detected changes in estimated leak flow to prevent undesired triggering of inspiration.

FIG. 1 is a diagram illustrating an embodiment of an exemplary ventilator 100 connected to a human patient 150. Ventilator 100 includes a pneumatic system 102 (also referred to as a pressure generating system 102) for circulating breathing gases to and from patient 150 via the ventilation tubing system 130, which couples the patient 150 to the pneumatic system 102 via an invasive (e.g., endotracheal tube, as shown) or a non-invasive (e.g., nasal mask) patient interface 180.

Ventilation tubing system 130 (or patient circuit 130) may be a two-limb (shown) or a one-limb circuit for carrying gases to and from the patient 150. In a two-limb embodiment, a fitting, typically referred to as a "wye-fitting" 170, may be provided to couple a patient interface 180 (as shown, an endotracheal tube) to an inspiratory limb 132 and an expiratory limb 134 of the ventilation tubing system 130.

Pneumatic system 102 may be configured in a variety of ways. In the present example, pneumatic system 102 includes an expiratory module 108 coupled with the expiratory limb 134 and an inspiratory module 104 coupled with the inspiratory limb 132. Compressor 106 or other source(s) of pressurized gases (e.g., air, oxygen, and/or helium) is coupled with inspiratory module 104 and the expiratory module 108 to provide a gas source for ventilatory support via inspiratory limb 132.

The inspiratory module 104 is configured to deliver gases to the patient 150 according to prescribed ventilatory settings. In some embodiments, inspiratory module 104 is configured to provide ventilation according to various breath types.

The expiratory module 108 is configured to release gases from the patient's lungs according to prescribed ventilatory settings. The expiratory module 108 is associated with and/or controls an expiratory valve for releasing gases from the patient 150. Further, the expiratory module 108 may instruct the pressure generating system 102 and/or the inspiratory module 104 to deliver a base flow during exhalation.

The ventilator 100 may also include one or more sensors 107 communicatively coupled to ventilator 100. The sensors 107 may be located in the pneumatic system 102, ventilation tubing system 130, and/or on the patient 150. The embodiment of FIG. 1 illustrates a sensor 107 in pneumatic system 102.

Sensors 107 may communicate with various components of ventilator 100, e.g., pneumatic system 102, other sensors 107, expiratory module 108, inspiratory module 104, processor 116, controller 110, trigger module 115, inspiratory trigger trajectory module 117 (illustrated as "ITT Module"), base flow trajectory module 118 (illustrated as "Base Flow Traj. Module"), Leak Estimation Module 119 (illustrated as "Leak Est. Module), and any other suitable components and/or modules. In one embodiment, sensors 107 generate output and send this output to pneumatic system 102, other sensors 107, expiratory module 108, inspiratory module 104, processor 116, controller 110, trigger module 115, inspiratory trigger trajectory module 117, base flow trajectory module 118, leak estimation module 119, and any other suitable components and/or modules.

Sensors 107 may employ any suitable sensory or derivative technique for monitoring one or more patient parameters or ventilator parameters associated with the ventilation of a patient 150. Sensors 107 may detect changes in patient parameters indicative of patient inspiratory or expiratory triggering, for example. Sensors 107 may be placed in any suitable location, e.g., within the ventilatory circuitry or other devices communicatively coupled to the ventilator 100. Further, sensors 107 may be placed in any suitable internal location, such as, within the ventilatory circuitry or within components or modules of ventilator 100. For example, sensors 107 may be coupled to the inspiratory and/or expiratory modules for detecting changes in, for example, circuit pressure and/or flow. In other examples, sensors 107 may be affixed to the ventilatory tubing or may be embedded in the tubing itself. According to some embodiments, sensors 107 may be provided at or near the lungs (or diaphragm) for detecting a pressure in the lungs. Additionally or alternatively, sensors 107 may be affixed or embedded in or near wye-fitting 170 and/or patient interface 180. Indeed, any sensory device useful for monitoring changes in measurable parameters during ventilatory treatment may be employed in accordance with embodiments described herein.

As should be appreciated, with reference to the Equation of Motion, ventilatory parameters are highly interrelated and, according to embodiments, may be either directly or indirectly monitored. That is, parameters may be directly monitored by one or more sensors 107, as described above, or may be indirectly monitored or estimated by derivation according to the Equation of Motion or other known relationships.

The pneumatic system 102 may include a variety of other components, including mixing modules, valves, tubing, accumulators, filters, etc. Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.).

In one embodiment, the operator interface 120 of the ventilator 100 includes a display 122 communicatively coupled to ventilator 100. Display 122 provides various input screens, for receiving clinician input, and various display screens, for presenting useful information to the clinician. In one embodiment, the display 122 is configured to include a graphical user interface (GUI). The GUI may be an interactive display, e.g., a touch-sensitive screen or otherwise, and may provide various windows and elements for receiving input and interface command operations. Alternatively, other suitable means of communication with the ventilator 100 may be provided, for instance by a wheel, keyboard, mouse, or other suitable interactive device. Thus, operator interface 120 may accept commands and input through display 122.

Display 122 may also provide useful information in the form of various ventilatory data regarding the physical condition of a patient 150. The useful information may be derived by the ventilator 100, based on data collected by a processor 116, and the useful information may be displayed to the clinician in the form of graphs, wave representations, pie graphs, text, or other suitable forms of graphic display. For example, patient data may be displayed on the GUI and/or display 122. Additionally or alternatively, patient data may be communicated to a remote monitoring system coupled via any suitable means to the ventilator 100. In some embodiments, the display 122 may illustrate a minimum exhalation flow, a minimum exhalation time, a maximum exhalation time, a desired base flow, a desired inspiratory trigger, an inspiratory trigger, a base flow, an exhalation flow, an estimated leak flow, an exhalation pressure, and/or any other information known, received, or stored by the ventilator 100.

In some embodiments, controller 110 includes memory 112, one or more processors 116, storage 114, and/or other components of the type commonly found in command and control computing devices. Controller 110 may further include an inspiratory trigger trajectory module 117, a base flow trajectory module 118, a trigger module 115, and/or a leak estimation module 119 as illustrated in FIG. 1. In alternative embodiments, the inspiratory trigger trajectory module 117, the base flow trajectory module 118, trigger module 115, and/or the leak estimation module 119 are located in other components of the ventilator 100, such as in the pressure generating system 102 (also known as the pneumatic system 102).

The memory 112 includes non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

The base flow trajectory module 118 determines the amount of base flow to deliver to the patient circuit tubing during exhalation. The base flow trajectory module 118 adjusts the base flow based on an estimated leak flow during exhalation. The base flow trajectory module 118 receives the estimated leak flow from another component of the ventilator 100, such as the controller 110, processor 116, and/or the leak estimation module 119.

The base flow trajectory module 118 delivers a constant base flow during a first portion of exhalation and then varies the base flow delivered during at least a part of a second portion of exhalation. Accordingly, the base flow trajectory module 118 determines an initial base flow to deliver during a first portion of exhalation. In some embodiments, the initial base flow is input or selected by the operator. In other embodiments, the initial base flow is determined by the ventilator 100 based on the configuration of the ventilator 100 and/or based on ventilator and/or patient parameters and settings. The first portion of exhalation includes at least the beginning or start of the exhalation period. In some embodiments, the first portion of exhalation is a minimum exhalation time. The "minimum exhalation time" as referred to herein is a predetermined amount of time in which it is unlikely that a patient would desire to begin inspiration or would attempt to trigger an inspiration. The base flow trajectory module 118 instructs the inspiratory module 104 to deliver the initial base flow at the beginning of inhalation. In further embodiments, the base flow trajectory module 118 delivers the initial base flow at the beginning of the first portion of exhalation or for the entire duration of the first portion of exhalation.

The base flow trajectory module 118 may also determine a desired base flow. In some embodiments, the desired base flow is input or selected by the operator. In other embodiments, the desired base flow is determined by the ventilator 100 based on the configuration of the ventilator 100 and/or based on ventilator and/or patient parameters.

The base flow trajectory module 118 instructs the inspiratory module 104 to change the delivered base flow from the initial base flow towards a first flow value, such as the desired base flow, during at least a second portion of exhalation. The second portion of exhalation does not overlap with the first portion of exhalation. Accordingly, the second portion of exhalation does not include the beginning of exhalation, but may begin immediately thereafter.

The second portion of exhalation starts or begins based on the occurrence of a condition. The base flow trajectory module 118 may determine the occurrence of the condition based on output received from sensors 107. Accordingly, in some embodiments, the base flow trajectory module 118 instructs the inspiratory module 104 to change the base flow from the initial base flow towards the desired base flow after determining the occurrence of a condition. In some embodiments, the condition includes determining that a minimum exhalation time has expired, determining that a monitored exhalation flow is below the minimum exhalation flow; determining that the monitored exhalation flow is below the minimum exhalation flow prior to expiration of a maximum exhalation time, and/or determining that the maximum exhalation time has expired. In other embodiments, the condition includes determining that a minimum exhalation time has expired and determining that either a monitored exhalation flow is below the minimum exhalation flow prior to expiration of a maximum exhalation time or the maximum exhalation time has expired. The maximum exhalation time is a predetermined amount of time after which it becomes highly likely that a patient would attempt to trigger inspiration. The minimum exhalation flow is a predetermined flow rate that when exhaled by the patient indicates that a patient is approaching the end of active exhalation. In some embodiments, the base flow trajectory module 118 instructs the inspiratory module 104 to change the delivered base flow from the initial base flow towards a first flow value at the start of a second portion of exhalation or, according to some embodiments, for the entire duration of the second portion exhalation.

In embodiments, the base flow trajectory module 118 instructs the inspiratory module 104 to change the base flow according to an exponential trajectory. In some embodiments, the exponential trajectory is based on a time constant that is indicative of the expected response time from the initial point to the final desired flow target. The time constant may be determined by the ventilator 100 based on the ventilator configuration or based on ventilator and/or patient parameters. In other embodiments, the time constant is input or selected by the operator.

In further embodiments, the base flow trajectory module 118 instructs the inspiratory module 104 to change the base flow until the delivered base flow is essentially or substantially the first flow value, such as a desired base flow. Once the delivered base flow substantially reaches the first flow value, the base flow trajectory module 118 instructs the inspiratory module 104 to deliver the first flow value. The first flow value is substantially reached or essentially reached when the ventilator 100 can no longer change the amount of base flow provided without reaching or exceeding the first flow value based on the sensitivity and precision of the ventilator components.

According to embodiments, if a change in leak size (leak flow rate) is detected during the exhalation phase (e.g., past the initial restricted period), the base flow should be adjusted accordingly. In this case, the base flow trajectory module 118 instructs the inspiratory module 104 to change the base flow in a smooth fashion (e.g., exponential ascend or descend) towards the desired level. In such cases, the duration of the transition as well as the initial magnitude for adjusting the trigger sensitivity is determined by the timeline of the transition of the base flow and the status of the patient's exhalation activity (e.g., the higher the patient's expiratory effort, the lower the probability of a new breath trigger).

Ventilators 100, depending on their mode of operation, may trigger automatically and/or in response to a detected change in a ventilator and/or patient parameter. The trigger module 115 receives and/or determines one or more inspiratory trigger thresholds. In some embodiments, the trigger module 115 receives an inspiratory trigger threshold from the ITT Module 117. In other embodiments, the trigger module 115 determines an inspiratory trigger threshold based on ventilator and/or patient parameters and/or the ventilator configuration. For example, the ventilator may be preconfigured to deliver an inspiration after a predetermined amount of exhalation time to prevent a patient from becoming under-ventilated. In other embodiments, the trigger module 115 receives an inspiratory trigger threshold from operator input or selection.

During exhalation, the trigger module 115 monitors ventilator and/or patient parameters and compares these parameters to one or more inspiratory trigger thresholds to determine if the parameters meet and/or exceed the inspiratory trigger thresholds. Sensors 107 suitable for this detection may include any suitable sensing device as known by a person of skill in the art for a ventilator 100. If the trigger module 115 determines that ventilator and/or patient parameters meet and/or exceed an inspiratory trigger threshold during exhalation, the trigger module 115 instructs the inspiratory module 104 to deliver an inspiration, which effectively ends the exhalation phase controlled by the expiratory module 108. If the trigger module 115 determines that ventilator and/or patient parameters do not meet and/or exceed an inspiratory trigger threshold during exhalation, the trigger module 115 continues to monitor the ventilator and/or patient parameters and compare them to a trigger threshold until the ventilator and/or patient parameters meet and/or exceed a trigger threshold.

In some embodiments, the trigger module 115 of the ventilator 100 detects changes in a ventilator and/or patient parameter via the monitoring of a respiratory gas pressure, the monitoring of lung flow, direct or indirect measurement of nerve impulses, or any other suitable method for detecting changes in a ventilator parameter for comparison to an inspiratory trigger threshold. In embodiments where changes in a ventilator parameter are detected by monitoring flow and/or pressure, the sensitivity of the ventilator 100 to changes in pressure and/or flow, may be adjusted. For example, the lower a pressure or flow change trigger threshold setting, the more sensitive the ventilator 100 may be to a patient initiated trigger. However, each ventilator 100 will have a minimum measurable inspiratory flow and thereby have a change in flow that the ventilator 100 cannot detect. Accordingly, a monitored parameter below a minimum measurable value will not be detected by the ventilator 100.

According to an embodiment, a pressure-triggering method may involve the trigger module 115 of the ventilator 100 monitoring the circuit pressure, and detecting a slight drop in circuit pressure. The slight drop in circuit pressure may indicate that the patient's respiratory muscles are creating a slight negative pressure that in turn generates a pressure gradient between the patient's lungs and the airway opening in an effort to inspire. The ventilator 100 may interpret the slight drop in circuit pressure as a patient trigger and may consequently initiate inspiration by delivering respiratory gases.

Alternatively, the trigger module 115 of the ventilator 100 may detect a flow-triggered event. Specifically, the trigger module 115 of the ventilator 100 may monitor the circuit flow, as described above. If the ventilator 100 detects a slight drop in the base flow through the exhalation module during exhalation, this may indicate that the patient 150 is attempting to inspire. In this case, the ventilator 100 is detecting a drop in base flow attributable to a slight redirection of gases into the patient's lungs (in response to a slightly negative pressure gradient as discussed above). Accordingly, changes in base flow as instructed by the base flow trajectory module 118 may, if the trigger threshold is set too low, trigger an unwanted inspiration.

The inspiratory trigger trajectory module 117 (illustrated as the "ITT Module") determines a patient initiated inspiratory trigger threshold. The ITT module 117 sends the determined inspiratory trigger threshold to another component of the ventilator, such as the controller 110, processor 116, and/or the trigger module 115. The trigger module 115, as discussed above, monitors the ventilator and/or patient parameters to determine if the parameters meet and/or exceed the inspiratory trigger threshold. The ITT module 117 continuously updates the inspiratory trigger threshold. Accordingly, the ITT module 117 may send different inspiratory trigger thresholds during different portions of exhalation.

The ITT module 117 determines and sets an initial inspiratory trigger threshold while delivering the initial base flow. In some embodiments, the initial inspiratory trigger threshold is input or selected by the operator. In other embodiments, the initial inspiratory trigger threshold is determined by the ventilator 100 based on the configuration of the ventilator and/or based on ventilator parameters and/or patient parameters. The initial inspiratory trigger is set during at least the first portion of exhalation, which includes at least the beginning or start of the exhalation period.

In some embodiments, in order to prevent undesirable early inspiratory triggers, the inspiratory trigger may be set relatively high. For example, in some embodiments, the initial inspiratory trigger requires a change of flow of at least 6 liters per minute (LPM). In other embodiments, the initial inspiratory trigger requires a change of flow of at least 8 LPM. In further embodiments, the initial inspiratory trigger requires a change of flow of at least 10 LPM.

Figure 4:
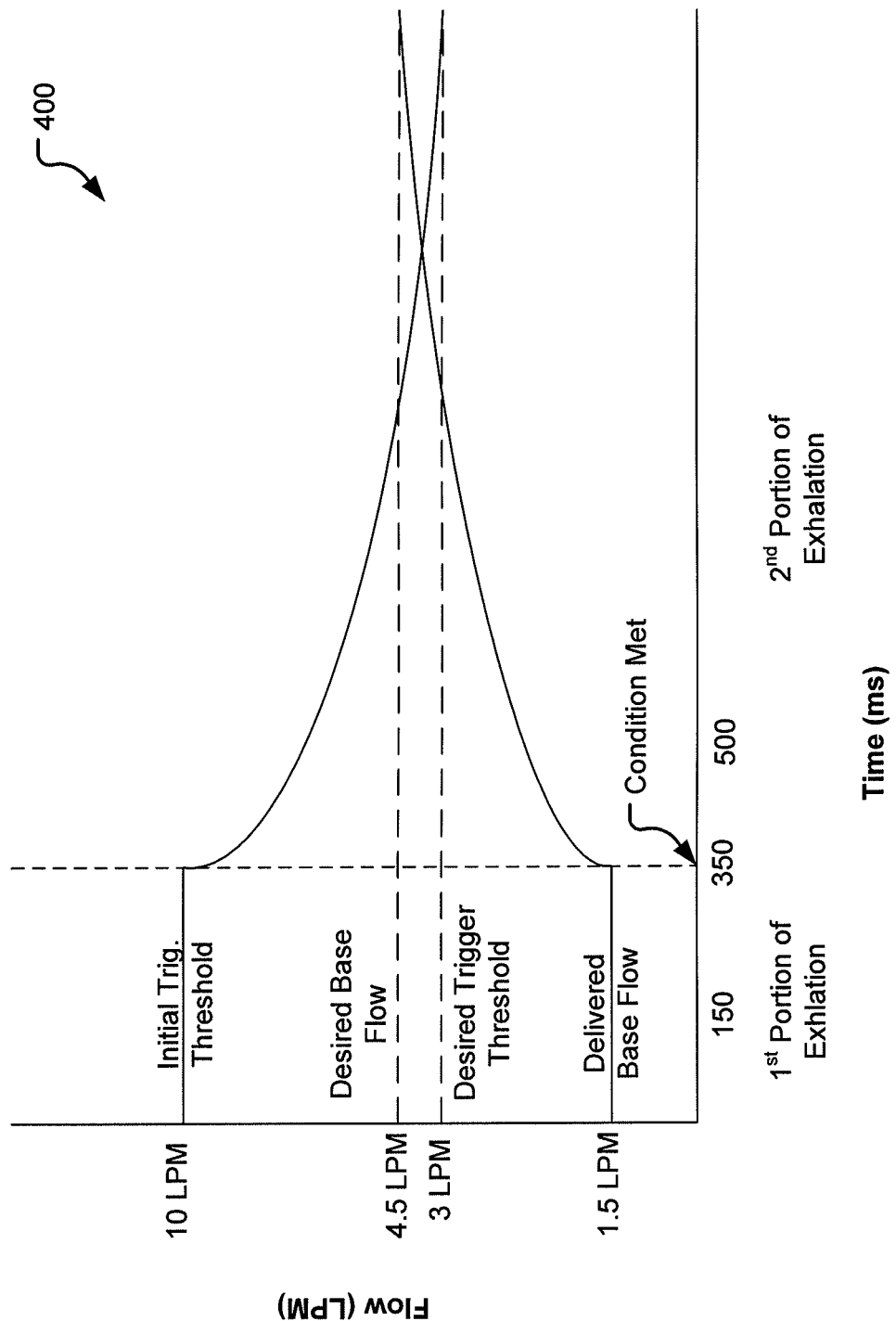
FIG. 4 illustrates an embodiment of a graph of delivered base flow and a set inspiratory trigger threshold over time during an exhalation.

However, as the exhalation continues the likelihood that a patient desires to initiate an inspiration increases. Accordingly, the ITT module 117 decreases an inspiratory trigger threshold during the second portion of exhalation. The decrease in the inspiratory trigger threshold requires a patient to make less of an effort to trigger a desired inspiration during the second portion of exhalation. Thus, the ITT module 117 decreases an inspiratory trigger threshold while the base flow trajectory module 118 changes the base flow delivered to the patient circuit tubing, as illustrated in FIG. 4.

In some embodiments, the ITT module 117 decreases the inspiratory trigger at an exponential trajectory. In some embodiments, the exponential trajectory is based on a time constant. The time constant may be determined by the ventilator 100 based on the ventilator configuration or based on ventilator and/or patient parameters. In other embodiments, the time constant is input or selected by the operator. In some embodiments, the time constant utilized by the ITT module 117 is the same time constant utilized by the base flow trajectory module 118 to determine how to change the amount of base flow delivered to the patient circuit tubing. In other embodiments, the ITT module 117 decreases an inspiratory trigger threshold as a function of the amount the base flow trajectory module 118 changes base flow or instructs the inspiratory module 104 to change base flow. In further embodiments, the ITT module 117 decreases an inspiratory trigger threshold concurrently while the base flow trajectory module 118 changes the base flow delivered to the patient circuit tubing, as illustrated in FIG. 4 (illustrating an increase in base flow concurrently with a decrease in the inspiratory trigger threshold).

In some embodiments, the ITT module 117 also determines a first inspiratory trigger threshold value, such as a desired inspiratory trigger threshold. In some embodiments, the first inspiratory trigger threshold value is input or selected by the operator. In other embodiments, the first inspiratory trigger threshold value is determined by the ventilator 100 based on the configuration of the ventilator 100 and/or based on ventilator parameters and/or patient parameters. In embodiments with a first inspiratory trigger threshold value, the ITT module 117 decreases the inspiratory trigger threshold from the initial inspiratory trigger threshold towards the first inspiratory trigger threshold value, such as a desired inspiratory trigger threshold.

Accordingly, in some embodiments, the ITT module 117 decreases the inspiratory trigger threshold until the inspiratory trigger essentially or substantially reaches the first inspiratory trigger threshold value. Once the inspiratory trigger threshold substantially reaches the first inspiratory trigger threshold value, the ITT module 117 sets the inspiratory trigger threshold value to the first inspiratory trigger threshold value. The first inspiratory trigger threshold value is substantially reached or essentially reached when the ventilator 100 can no longer decrease the inspiratory trigger threshold without reaching or passing the first inspiratory trigger threshold value based on the sensitivity and precision of the ventilator components.

According to some embodiments, the base flow trajectory module 118 allows the ventilator 100 to provide a lower base flow during a first portion of exhalation and a higher base flow during a second portion of exhalation or vice versa. When the ventilator delivers a lower base flow during active exhalation (i.e., the first portion of exhalation), there is less uncertainty caused by measuring base flow at different sensors 107 (once on the delivery side and a second time as a portion of exhaust gas on the exhalation side). This is particularly advantageous under neonatal conditions when tidal volumes and exhaled flow rates are relatively smaller and may be some orders of magnitude smaller than the base flow. Accordingly, the base flow trajectory module 118 allows the processor 116 or controller 110 to more accurately calculate exhaled tidal volume and/or spirometry than ventilators that utilize a constant base flow or a higher amount of base-flow during active exhalation.

The leak estimation module 119 estimates the amount of flow leaking from the ventilation tubing system 130. The leak estimation module 119 sends the estimated leak flow to other components of the ventilator 100, such as the controller 110, processor 116, base flow trajectory module 118, pneumatic system 102, and/or display 122.

According to embodiments, the initial base flow includes the estimated leak flow determined by leak estimation module 119. In some embodiments, the initial base flow is zero if there is no estimated leak flow and no desired initial base flow. In alternative embodiments, the initial base flow is at least equivalent to or greater than the estimated leak flow. The leak estimation module 119 estimates the amount of flow leaking from the ventilation tubing system 130 by utilizing any conventionally known method for estimating leak flow from the ventilation tubing system 130. Additionally, with reference to embodiments described above, the first flow value includes the estimated leak flow as determined by the leak estimation module 119 to compensate for the amount of flow lost from the ventilation tubing system 130 during ventilation. Moreover, according to embodiments, the base flow trajectory module 118 utilizes the estimated leak flow, as determined by the leak estimation module 119, to determine the initial base flow and/or the first flow value.

Further, the leak estimation module 119 determines if there has been a change in the estimated leak flow during exhalation. In some embodiments, after a change in the estimated leak flow has been detected, the leak estimation module 119 updates the estimated leak flow based on the detected change. In embodiments, the leak estimation module 119 determines if there has been a change in the estimated leak flow during exhalation by monitoring one or more patient and/or ventilator parameters or settings. In further embodiments, the leak estimation module 119 determines if there has been a change in the estimated leak flow during exhalation by monitoring output from one or more sensors 107. The leak estimation module 119 determines a change in the amount of flow leaking from the ventilation tubing system 130 during exhalation by utilizing any conventionally known method for estimating leak flow and/or for detecting a change in the leak flow from the ventilation tubing system 130. The leak estimation module 119 sends the determined change in the estimated leak flow (or an updated estimated leak flow value) to other components of the ventilator 100, such as the controller 110, processor 116, base flow trajectory module 118, ITT module 117, pneumatic system 102, and/or display 122.

According to embodiments, a change in leak flow during exhalation can impact the base flow during exhalation, resulting in too much or too little base flow during exhalation and causing patient discomfort and/or inaccurate triggering. Accordingly, the determined change in estimated leak flow is utilized by the base flow trajectory module 118 to adjust the base flow during exhalation. For example, if an increase in estimated leak flow is detected during exhalation, base flow may be increased. Alternatively, if a decrease in the estimated leak flow is detected during exhalation, base flow may be decreased.

According to further embodiments, when the base flow trajectory module 118 receives a determined change in the estimated leak flow, the base flow trajectory module 118 progressively adjusts the base flow delivered during exhalation during a set time period to compensate for the determined change. The base flow trajectory module 118 may increase or decrease the delivered base flow during exhalation depending upon the determined change in the estimated leak flow. As used herein "progressively adjust" refers to changing the base flow delivered in a plurality of increments during a set time period to compensate for the detected change in estimated leak flow. For example, the base flow trajectory module 118 may change the amount of base flow delivered over the set time period in phases, in a step-wise pattern, and/or utilizing an exponential trajectory.

In some embodiments, the base flow is progressively adjusted utilizing an exponential trajectory based on a time constant. The time constant may be the same time constant utilized by the ventilator during the second phase of exhalation to change the delivered base flow and/or to decrease the inspiratory trigger threshold. In some embodiments, the ventilator determines the time constant. In other embodiments, the time constant is selected or input by an operator.

In alternative embodiments, the base flow is progressively adjusted as a function of the determined change in the estimated leak flow. In some embodiments, the base flow is progressively adjusted based on percentage multiplied by the determined change in the estimated leak flow, such as a percentage of 5%, 10%, 15%, 20%, 25%, etc. For example, if the estimated leak flow increases by 5 liters per min (LPM), the base flow trajectory module 118 may progressively adjust the base flow delivered during exhalation during the set time period by 10% increments, e.g., progressively increase the delivered base flow by increments of 0.50 LPM over the set time period until the base flow is increased by the 5 LPM increase in estimated leak flow.

In some embodiments, the set time period is determined by the ventilator 100. In some embodiments, the set time period is based on the configuration of the ventilator. In other embodiments, the set time period is determined by the ventilator based on ventilator and/or patient parameters or settings. In some embodiments, the set time period determined by the ventilator is a function of the determined change in the estimated leak flow. In alternative embodiments, the set time period is selected or input by the operator. Is some embodiments, the set time period is 200 milliseconds (ms) or less. In other embodiments, the set time period is 150 ms or less. In other embodiments, the set time period is 125 ms or less.

When the ITT module 117 receives a determined change in the estimated leak flow, the ITT module 117 adjusts the inspiratory trigger threshold for the set time period. For example, if the estimated leak flow increases (resulting in a decreased base flow through the exhalation module), the inspiratory trigger threshold may also be increased, thereby decreasing trigger sensitivity and making it less probable for a false determination of the patient inspiratory trigger. Alternatively, if the estimated leak flow decreases (resulting in an increase in base flow through the exhalation module), the inspiratory trigger threshold may also be decreased for a transition period, thereby increasing the probability of detecting the patient's effort to trigger inspiration.

In some embodiments, the inspiratory trigger threshold is increased based on a function of a detected increase in estimated leak flow. In this case, according to embodiments, the inspiratory trigger is increased one time by a set amount for the duration of the set time period. In alternative embodiments, the ITT module 117 progressively increases the inspiratory trigger threshold for the set time period. As used herein "progressively increases" refers to increasing the inspiratory trigger threshold in a plurality of increments during the set time period. For example, the ITT module 117 may increase the inspiratory trigger threshold during the set time period in phases, in a step-wise pattern, and/or by utilizing an exponential trajectory.

In further embodiments, the inspiratory trigger threshold is progressively increased utilizing an exponential trajectory based on a time constant. The time constant may be the same time constant utilized by the ventilator during the second phase of exhalation to increase the delivered base flow and/or to decrease the inspiratory trigger threshold. In some embodiments, the ventilator determines the time constant. In other embodiments, the time constant is selected or input by an operator.

In some embodiments, the inspiratory trigger threshold is increased based on a percentage multiplied by the determined increase in the estimated leak flow, such as a percentage of 5%, 10%, 15%, 20%, 25%, etc. For example, if the estimated leak flow increases by 5 liters per minute (LPM) (decreasing base flow), the ITT module 117 may increase the inspiratory trigger threshold by 10% increments over a set time period during exhalation, e.g., 0.5 LPM each cycle, until the inspiratory trigger threshold is increased by 5 LPM. According to embodiments, the ITT module 117 may increase the inspiratory trigger threshold according to any suitable percentage, algorithm, protocol, etc.

According to alternative embodiments, the inspiratory trigger threshold is decreased as a function of a detected decrease in estimated leak flow. In this case, the inspiratory trigger may be decreased one time by a set amount for the duration of the set time period. In alternative embodiments, the ITT module 117 progressively decreases the inspiratory trigger threshold for the set time period. As used herein "progressively decreases" refers to decreasing the inspiratory trigger threshold in a plurality of increments during the set time period. For example, the ITT module 117 may decrease the inspiratory trigger threshold during the set time period in phases, in a step-wise pattern, and/or by utilizing an exponential trajectory.

In further embodiments, the inspiratory trigger threshold is progressively decreased utilizing an exponential trajectory based on a time constant. The time constant may be the same time constant utilized by the ventilator during the second phase of exhalation to change the delivered base flow and/or to decrease the inspiratory trigger threshold. In some embodiments, the ventilator determines the time constant. In other embodiments, the time constant is selected or input by an operator.

In some embodiments, the inspiratory trigger threshold is decreased based on a percentage multiplied by the determined decrease in the estimated leak flow, such as a percentage of 5%, 10%, 15%, 20%, 25%, etc. For example, if the estimated leak flow decreases by 5 liters per minute (LPM) (decreasing base flow), the ITT module 117 may decrease the inspiratory trigger threshold by 10% increments over a set time period during exhalation, e.g., 0.5 LPM each cycle, until the inspiratory trigger threshold is decreased by 5 LPM. According to embodiments, the ITT module 117 may decrease the inspiratory trigger threshold according to any suitable percentage, algorithm, protocol, etc.

According to alternative embodiments, during a second portion of exhalation, the ITT Module 117 decreases the inspiratory trigger threshold when the base flow is changed. During the second portion of exhalation, it is more likely that the patient will trigger a desired inspiration. As such, decreasing the inspiratory trigger threshold increases trigger sensitivity and makes it easier for the patient to trigger inspiration. According to additional embodiments, ITT Module 117 adaptively adjusts the inspiratory trigger threshold during the second period of exhalation based on detecting a change in estimated leak flow. That is, while the inspiratory trigger threshold may follow a generally declining exponential trajectory during the second portion of exhalation, this declining exponential may be adjusted based on detecting a change in the estimated leak flow (i.e., increasing the inspiratory trigger threshold upon detecting an increase in estimated leak flow and decreasing the inspiratory trigger threshold upon detecting a decrease in estimated leak flow during the second portion of exhalation).

Figure 2:
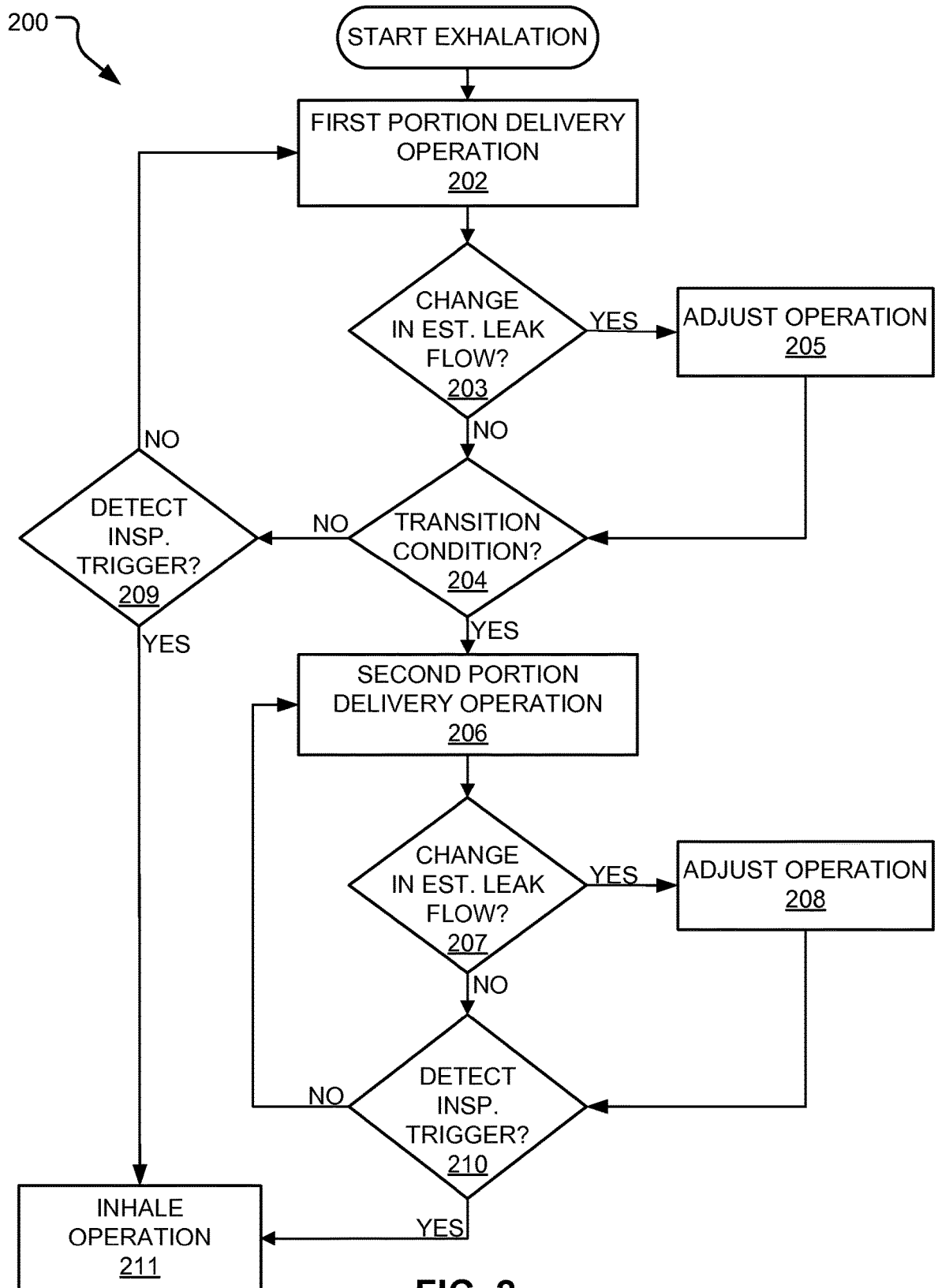
FIG. 2 illustrates an embodiment of a method for ventilating a patient on a ventilator.

FIG. 2 illustrates an embodiment of a method 200 for ventilating a patient with a ventilator. Method 200 begins at the start of exhalation. During exhalation the ventilator delivers a base flow to a patient. The base flow includes an estimated leak flow. According to embodiments, during a first portion of exhalation the ventilator delivers an initial base flow to the patient circuit tubing. According to further embodiments, during a second portion of exhalation, the ventilator delivers an adaptive base flow that changes exponentially from the initial base flow toward a desired base flow. Additionally, during exhalation the ventilator determines and sets an inspiratory trigger threshold. For example, during exhalation the ventilator determines an initial inspiratory trigger threshold and a desired inspiratory trigger threshold. According to embodiments, during a first portion of exhalation the ventilator sets an initial inspiratory trigger threshold. According to further embodiments, during a second portion of exhalation the ventilator configures the inspiratory trigger threshold to decrease exponentially from the initial inspiratory trigger threshold toward a desired inspiratory trigger threshold.

As illustrated, method 200 includes a first portion delivery operation 202. According to embodiments, the first portion of exhalation includes at least the beginning or start of exhalation and does not overlap with a second portion of exhalation. In some embodiments, the first portion of exhalation includes a minimum exhalation time.

According to embodiments, the ventilator delivers an initial base flow to the patient at the start of or for the entire duration of a first portion of exhalation during first portion delivery operation 202. The initial base flow includes an estimated leak flow. According to embodiments, the initial base flow may be predetermined by the ventilator based on the configuration of the ventilator or determined by the ventilator based on ventilator and/or patient parameters or settings. In an alternative embodiment, the initial base flow may be input or selected by an operator. According to further embodiments, the initial base flow is automatically adjusted to account for an estimated leak flow. According to embodiments, an amount of flow is added to the estimated leak flow in order to determine the initial base flow. According to embodiments, the amount of flow added may be predetermined by the ventilator based on the configuration of the ventilator or may be determined by the ventilator based on ventilator and/or patient parameters or settings. In an alternative embodiment, the amount of flow added to the estimated leak flow to determine the initial base flow is input or selected by an operator.

According to additional embodiments, the ventilator during the first portion delivery operation 202 determines an initial inspiratory trigger threshold for the first portion of exhalation. According to embodiments, the initial inspiratory trigger threshold may be predetermined by the ventilator based on the configuration of the ventilator or determined by the ventilator based on ventilator and/or patient parameters or settings. In an alternative embodiment, the initial inspiratory trigger threshold may be input or selected by an operator.

In some embodiments, the initial base flow is a base flow of zero or close to zero when the estimated leak flow is zero or close to zero. In alternative embodiments, the initial base flow is at least equivalent to or greater than the estimated leak flow. In some embodiments, the initial inspiratory trigger threshold is set relatively high. During early exhalation it is unlikely that a patient actually desires to trigger an inspiration. Accordingly, to prevent monitored parameters from resulting in a false trigger of an undesired inspiration, a high initial inspiratory trigger threshold may be utilized. For example, the initial inspiratory trigger threshold may require a change of flow of at least 6 to 10 LPM.

As illustrated, method 200 includes a change in estimated leak flow decision operation 203 (illustrated as "Change in Est. Leak Flow?"). The ventilator during the change in estimated leak flow decision operation 203 determines if there has been a change in the estimated leak flow. The ventilator monitors patient and/or ventilator parameters to determine if there has been a change in the estimated leak flow during exhalation. The estimated leak flow may be estimated by utilizing any known suitable methods or systems.

In some embodiments, method 200 detects changes in a ventilator and/or patient parameter via monitoring of a respiratory gas pressure, the monitoring of lung flow, direct or indirect measurement of nerve impulses, or any other suitable method for detecting changes in a ventilator and/or patient parameters. Method 200 may utilize sensors to monitor the ventilator and/or patient parameters. Sensors may include any suitable sensing device as known by a person of skill in the art for a ventilator. In some embodiments, the ventilator monitors the ventilator and/or patient parameters every computational cycle (e.g., 2 milliseconds, 5 milliseconds, 10 milliseconds, etc.) during the delivery of exhalation to determine if estimated leak flow has changed during exhalation.

If the ventilator during change in estimated leak flow decision operation 203 determines that there has been a change in the estimated leak flow, the ventilator selects to perform adjust operation 205. If the ventilator during change in estimated leak flow decision operation 203 determines that there has not been a change in the estimated leak flow, the ventilator selects to perform transition condition decision operation 204.

Method 200 also includes an adjust operation 205. The ventilator during adjust operation 205 progressively adjusts the initial base flow during a set time period during exhalation to compensate for the determined change in the estimated leak flow while also adjusting the inspiratory trigger threshold for the set time period. For example, if the ventilator determines estimated leak flow has increased (insufficient initial base flow), the ventilator may increase the initial base flow to compensate for the increase in estimated leak flow. Alternatively, if the ventilator determines estimated leak flow has decreased (excessive initial base flow), the ventilator may decrease the initial base flow to compensate for the decrease in estimated leak flow. In some embodiments, after a change in the estimated leak has been detected, ventilator during the adjust operation 205 further estimates the updated estimated leak flow based on the detected change during exhalation.

According to embodiments, the ventilator during adjust operation 205 may increase or decrease the initial base flow during exhalation depending on the determined change in the estimated leak flow. As used herein "progressively adjusted" refers to incrementally changing the initial base flow delivered during a set time period over a plurality of control cycles (e.g., 2 ms control cycles, 5 ms control cycles, etc.) to compensate for the detected change in estimated leak flow. For example, the ventilator during adjust operation 205 may change the amount of initial base flow delivered during the set time period in phases, in a step-wise pattern, and/or utilizing an exponential trajectory. The set time period for adjusting the initial base flow may be determined by the ventilator, e.g., based on pre-established ventilator settings or based on ventilator calculations. In alternative embodiments, the set time period is selected or input by the operator. In some embodiments, as described above, the initial base flow is progressively adjusted (increased or decreased) utilizing an exponential trajectory based on a time constant. In other embodiments, the initial base flow is adjusted (increased or decreased) based on a percentage multiplied by the determined change in the estimated leak flow, such as a percentage of 5%, 10%, 15%, 20%, 25%, etc. According to embodiments, the initial base flow may be increased according to any suitable percentage, algorithm, protocol, etc.

In additional embodiments, during adjust operation 205 the initial inspiratory trigger threshold is adjusted (increased or decreased) as a function of the detected change (increase or decrease) in estimated leak flow. For example, if the ventilator determines estimated leak flow has increased (decreasing the initial base flow), the ventilator may increase the initial inspiratory trigger threshold to compensate for the increase in estimated leak flow. In this case, the trigger sensitivity is decreased making it more difficult for the patient to trigger inspiration. Alternatively, if the ventilator determines estimated leak flow has decreased (increasing the initial base flow), the ventilator may decrease the initial inspiratory trigger threshold to compensate for the decrease in estimated leak flow. In this case, the trigger sensitivity is increased making it easier for the patient to trigger inspiration.

According to further embodiments, the ventilator during adjust operation 205 may increase or decrease the initial inspiratory trigger threshold during exhalation depending on the determined change in the estimated leak flow. As used herein "progressively adjusted" refers to incrementally changing the initial inspiratory trigger threshold delivered during a set time period over a plurality of control cycles (e.g., 2 ms control cycles, 5 ms control cycles, etc.) to compensate for the detected change in estimated leak flow. For example, the ventilator during adjust operation 205 may change the initial inspiratory trigger threshold during the set time period in phases, in a step-wise pattern, and/or utilizing an exponential trajectory. The set time period for adjusting the initial base flow may be determined by the ventilator or selected or input by the operator. In some embodiments, as described above, the initial inspiratory trigger threshold is progressively adjusted (increased or decreased) utilizing an exponential trajectory based on a time constant. In other embodiments, the initial inspiratory trigger threshold is adjusted (increased or decreased) based on a percentage multiplied by the determined change in the estimated leak flow, such as a percentage of 5%, 10%, 15%, 20%, 25%, etc. According to embodiments, the initial inspiratory trigger threshold may be increased according to any suitable percentage, algorithm, protocol, etc.

Further, method 200 includes a transition condition decision operation 204 (illustrated as "transition condition?"). During the transition condition decision operation 204, the ventilator determines if a condition has been met. The condition may include any suitable condition, including determining that a minimum exhalation time has expired, determining that an exhalation flow is below the minimum exhalation flow, determining that the exhalation flow is below the minimum exhalation flow prior to expiration of a maximum exhalation time, and/or determining that the maximum exhalation time has expired. The first portion of exhalation ends when the condition has been met. The second portion of exhalation begins when the condition has been met.

According to embodiments, if the ventilator during transition condition decision operation 204 determines that a condition has been met, the ventilator selects to perform second portion delivery operation 206. If the ventilator during transition condition decision operation 204 determines that a condition has not been met, the ventilator selects to perform inspiratory trigger decision operation 209.

According to embodiments, during the second portion delivery operation 206, the ventilator changes (i.e., increases or decreases) the base flow delivered to the patient tubing from the initial base flow toward a desired base flow during the second portion of exhalation. According to embodiments, the desired base flow is received via input or selection by an operator, e.g., via a graphical user interface, keyboard, mouse, and/or any other suitable input device for receiving and interpreting operator commands, instructions, and/or selections. In an alternative embodiment, the desired base flow is determined by the ventilator.

In some embodiments, the ventilator changes base flow from the initial base flow toward the desired base flow at the start of or during the entire duration of the second portion of exhalation. According to alternative embodiments, the ventilator incrementally changes the base flow from the initial base flow toward the desired base flow over a period of time. For example, the ventilator may incrementally change the base flow from the initial base flow toward the desired base flow in phases, in a step-wise pattern, and/or by utilizing an exponential trajectory. That is, the ventilator may incrementally change the base flow from the initial base flow toward the desired base flow to a first flow value in a first control cycle and to a second flow value in a second control cycle, etc.

In some embodiments, the ventilator during second portion delivery operation 206 changes the base flow from the initial base flow toward the desired base flow until the desired base flow is reached or substantially reached. If the delivered base flow reaches or substantially reaches the desired base flow, the ventilator during second portion delivery operation 206 delivers the desired base flow until inspiration is triggered by the patient. In some embodiments, the ventilator during second portion delivery operation 206 changes the base flow according to an exponential trajectory. In further embodiments, the ventilator during second portion delivery operation 206 changes the base flow according to an exponential trajectory based on a time constant. The time constant may be determined by the ventilator or input or selected by an operator.

Further, during the second portion delivery operation 206, the ventilator decreases an inspiratory trigger threshold from the initial inspiratory trigger threshold toward a desired inspiratory trigger threshold during at least a portion of the second portion of exhalation. Accordingly, in some embodiments, the ventilator concurrently or simultaneously changes the delivered base flow as the ventilator lowers the inspiratory trigger threshold during the second portion delivery operation 206.

In some embodiments, the ventilator during second portion delivery operation 206 decreases the inspiratory trigger threshold from the initial inspiratory trigger threshold towards the desired inspiratory trigger threshold until the desired inspiratory trigger threshold is reached or substantially reached. If the inspiratory trigger threshold reaches or substantially reaches the desired inspiratory trigger threshold, the ventilator during second portion delivery operation 206 maintains the inspiratory trigger threshold at the desired inspiratory trigger threshold until the patient triggers inspiration.

According to embodiments, the ventilator during second portion delivery operation 206 decreases the inspiratory trigger threshold at the start of or during the entire duration of the second portion of exhalation. According to alternative embodiments, the ventilator incrementally decreases the inspiratory trigger threshold from the initial inspiratory trigger threshold towards the desired inspiratory trigger threshold over a period of time. For example, the ventilator may incrementally decrease the inspiratory trigger threshold from the initial inspiratory trigger threshold towards the desired inspiratory trigger threshold in phases, in a step-wise pattern, and/or by utilizing an exponential trajectory. That is, the ventilator may incrementally decrease the inspiratory trigger threshold from the initial inspiratory trigger threshold towards the desired inspiratory trigger threshold to a first flow value in a first control cycle and to a second flow value in a second control cycle, etc.

In some embodiments, the ventilator during second portion delivery operation 206 decreases the inspiratory trigger threshold according to an exponential trajectory. In further embodiments, the ventilator during second portion delivery operation 206 decreases the inspiratory trigger threshold at an exponential trajectory based on a time constant. In some embodiments, the time constant is determined by the ventilator or input or selected by an operator. In further embodiments, the time constant may be the same time constant utilized by the ventilator to determine the amount to change the delivered base flow. In additional embodiments, the ventilator during second portion delivery operation 206 decreases the inspiratory trigger threshold as a function of the amount the ventilator changes the delivered base flow.

In some embodiments, the ventilator may decrease the inspiratory trigger threshold from the initial inspiratory trigger threshold towards the desired inspiratory trigger threshold until the desired inspiratory trigger threshold is substantially reached. If the set inspiratory trigger threshold reaches or substantially reaches the desired inspiratory trigger threshold, the ventilator during second portion delivery operation 206 maintains the inspiratory trigger threshold at the desired inspiratory trigger threshold until the patient triggers inspiration.

That is, method 200 decreases the inspiratory trigger threshold while the base flow is being changed. According to embodiments, the longer the exhalation period, the more likely the patient will attempt to initiate an inspiratory trigger. As such, decreasing the inspiratory trigger threshold during the second portion of exhalation allows a patient to exert less effort to trigger a desired inspiration when it becomes more likely that a patient will attempt to trigger an inspiration.

As illustrated, method 200 includes a change in estimated leak flow decision operation 207 (illustrated as "Change in Est. Leak Flow?"). Change in estimated leak flow decision operation 207 is substantially that same as change in estimated leak flow decision operation 203, described above. That is, at change in estimated leak flow decision operation 207 the ventilator determines if there has been a change in the estimated leak flow via any suitable means.

If the ventilator during change in estimated leak flow decision operation 207 determines that there has been a change in the estimated leak flow, the ventilator selects to perform adjust operation 208. If the ventilator during change in estimated leak flow decision operation 207 determines that there has not been a change in the estimated leak flow, the ventilator selects to perform detect inspiratory trigger decision operation 210.

At adjust operation 208, the ventilator progressively adjusts the base flow during a set time period during the second period of exhalation to compensate for the determined change in the estimated leak flow. For example, if the ventilator determines estimated leak flow has increased (insufficient base flow), the ventilator may increase the base flow to compensate for the increase in estimated leak flow. Alternatively, if the ventilator determines estimated leak flow has decreased (excessive base flow), the ventilator may decrease the base flow to compensate for the decrease in estimated leak flow. According to embodiments, during the second portion of exhalation, base flow is adjusted from an initial base flow to a desired base flow while also being adjusted based on detecting a change in estimated leak flow.

Additionally, during adjust operation 208 the ventilator progressively adjusts the inspiratory trigger threshold during the set time period to compensate for the determined change in the estimated leak flow. For example, if the ventilator determines estimated leak flow has increased (insufficient base flow), the ventilator may increase the inspiratory trigger threshold to compensate for the increase in estimated leak flow. Alternatively, if the ventilator determines estimated leak flow has decreased (excessive base flow), the ventilator may decrease the inspiratory trigger threshold to compensate for the decrease in estimated leak flow. According to embodiments, during the second portion of exhalation, inspiratory trigger threshold is adjusted from an initial inspiratory trigger threshold to a desired inspiratory trigger threshold while also being adjusted based on detecting a change in estimated leak flow.

As illustrated, method 200 includes an inspiratory trigger decision operation 209 (illustrated as "Detect Insp. Trigger?"). During the inspiratory trigger decision operation 209, the ventilator determines if an inspiratory trigger has been detected. Inspiratory trigger decision operation 209 is performed during the first portion of exhalation.

The ventilator, during inspiratory trigger decision operation 209, monitors patient and/or ventilator parameters or settings to determine if an inspiratory trigger threshold has been met and/or exceeded during the first portion of exhalation. The inspiratory trigger threshold includes any suitable condition or threshold for determining that inspiration should be provided to the patient. During the first portion of exhalation, the inspiratory trigger threshold includes the initial inspiratory trigger threshold as determined by first portion delivery operation 202.

In some embodiments, method 200 detects changes in a ventilator and/or patient parameter via the monitoring of a respiratory gas pressure, the monitoring of lung flow, direct or indirect measurement of nerve impulses, or any other suitable method for detecting changes in a ventilator parameter for comparison to inspiratory trigger thresholds. Method 200 may utilize sensors to monitor the ventilator and/or patient parameters. Sensors may include any suitable sensing device as known by a person of skill in the art for a ventilator. In some embodiments, the inspiratory trigger threshold may be a change in exhalation pressure or a change in exhalation flow. In some embodiments, the sensors are located in the pneumatic system, the breathing circuit, and/or at the patient. In some embodiments, the ventilator monitors the exhalation flow and/or exhalation pressure every computational cycle (e.g., 2 milliseconds, 5 milliseconds, 10 milliseconds, etc.) during the delivery of exhalation to determine if the inspiratory trigger threshold has been met and/or exceeded.

If the ventilator during inspiratory trigger decision operation 209 determines that the ventilator and/or patient parameters do not meet or exceed an inspiratory trigger threshold, the ventilator selects to perform first portion delivery operation 202. If the ventilator during inspiratory trigger decision operation 209 determines that the ventilator and/or patient parameters do meet or exceed an inspiratory trigger threshold, the ventilator selects to perform inhale operation 211. The performance of the inhale operation 211 ends the exhalation phase.

Method 200 includes an inspiratory trigger decision operation 210 (illustrated as "Detect Insp. Trigger?"). During the inspiratory trigger decision operation 210, similar to inspiratory trigger decision operation 209, the ventilator determines if an inspiratory trigger has been detected. Inspiratory trigger decision operation 210 is performed during the second portion of exhalation.

The ventilator, during inspiratory trigger decision operation 210, monitors patient and/or ventilator parameters or settings to determine if an inspiratory trigger threshold has been met and/or exceeded during the second portion of exhalation. The inspiratory trigger threshold includes any suitable condition or threshold for determining that inspiration should be provided to the patient. During the second portion of exhalation, the inspiratory trigger threshold includes an inspiratory trigger threshold substantially equal to or declining toward the desired inspiratory trigger threshold as determined by second portion delivery operation 206.

If the ventilator during inspiratory trigger decision operation 210 determines that the ventilator and/or patient parameters do not meet or exceed an inspiratory trigger threshold, the ventilator selects to perform second portion delivery operation 206. If the ventilator during inspiratory trigger decision operation 210 determines that the ventilator and/or patient parameters do meet or exceed an inspiratory trigger threshold, the ventilator selects to perform inhale operation 211. The performance of the inhale operation 211 ends the exhalation phase.

In additional embodiments, method 200 includes a display operation. The ventilator during the display operation displays any suitable information for display on a ventilator. In one embodiment, the display operation displays at least one of a minimum exhalation flow, a minimum exhalation time, a maximum exhalation time, a desired base flow, an initial base flow, a desired inspiration trigger threshold, an initial inspiratory trigger threshold, an exhalation flow, an estimated leak flow, and an exhalation pressure.

Accordingly, in some embodiments, method 200 further includes a calculation operation. The ventilator during the calculation operation calculates an exhaled tidal volume. The ventilator may utilize any known methods for calculating exhaled tidal volume. In some embodiments, the ventilator during the calculation operation also calculates spirometry. In some embodiments, the spirometry calculation is based on the calculated exhaled tidal volume. The ventilator may utilize any known methods for calculating spirometry.

In some embodiments, a microprocessor-based ventilator that accesses a computer-readable medium having computer-executable instructions for performing the method of ventilating a patient with a medical ventilator is disclosed. This method includes repeatedly performing the steps disclosed in method 200 above and/or as illustrated in FIG. 2.

In some embodiments, the ventilator system includes: means for determining an initial base flow; means for determining an initial inspiratory trigger threshold; means for delivering the initial base flow during at least a first portion of exhalation while setting the inspiratory trigger threshold to the initial inspiratory trigger threshold; means for changing base flow from the initial base flow toward a first flow value during at least a second portion of exhalation; and means for decreasing the inspiratory trigger threshold from the initial inspiratory trigger threshold toward a first trigger threshold value while performing the step of changing the base flow.

As should be appreciated, the particular steps and methods described herein are not exclusive and, as will be understood by those skilled in the art, the particular ordering of steps as described herein is not intended to limit the method, e.g., steps may be performed in differing order, additional steps may be performed, and disclosed steps may be excluded without departing from the spirit of the present methods.

Figure 3A:
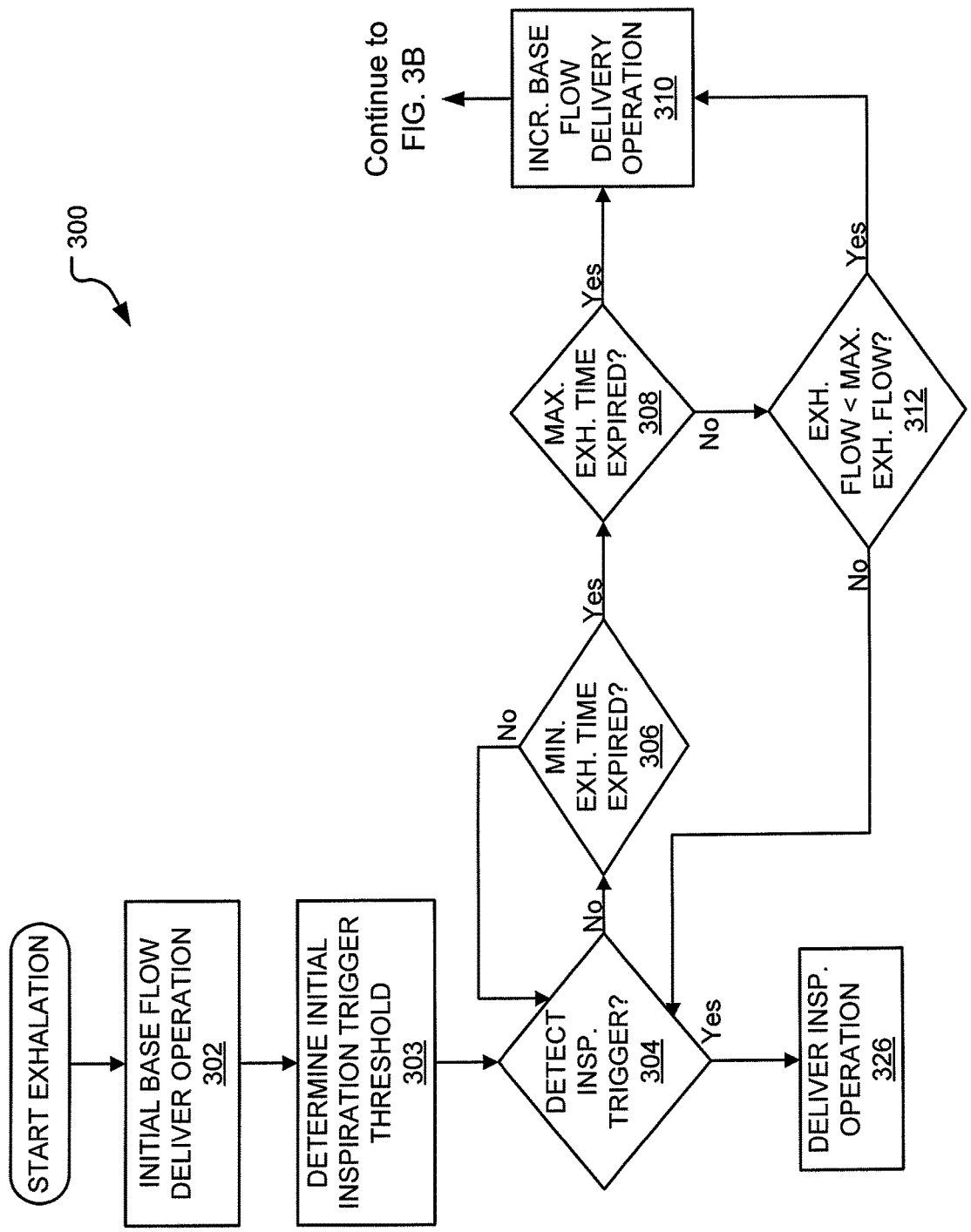
FIG. 3A illustrates an embodiment of a first portion of a method for ventilating a patient on a ventilator.
Figure 3B:
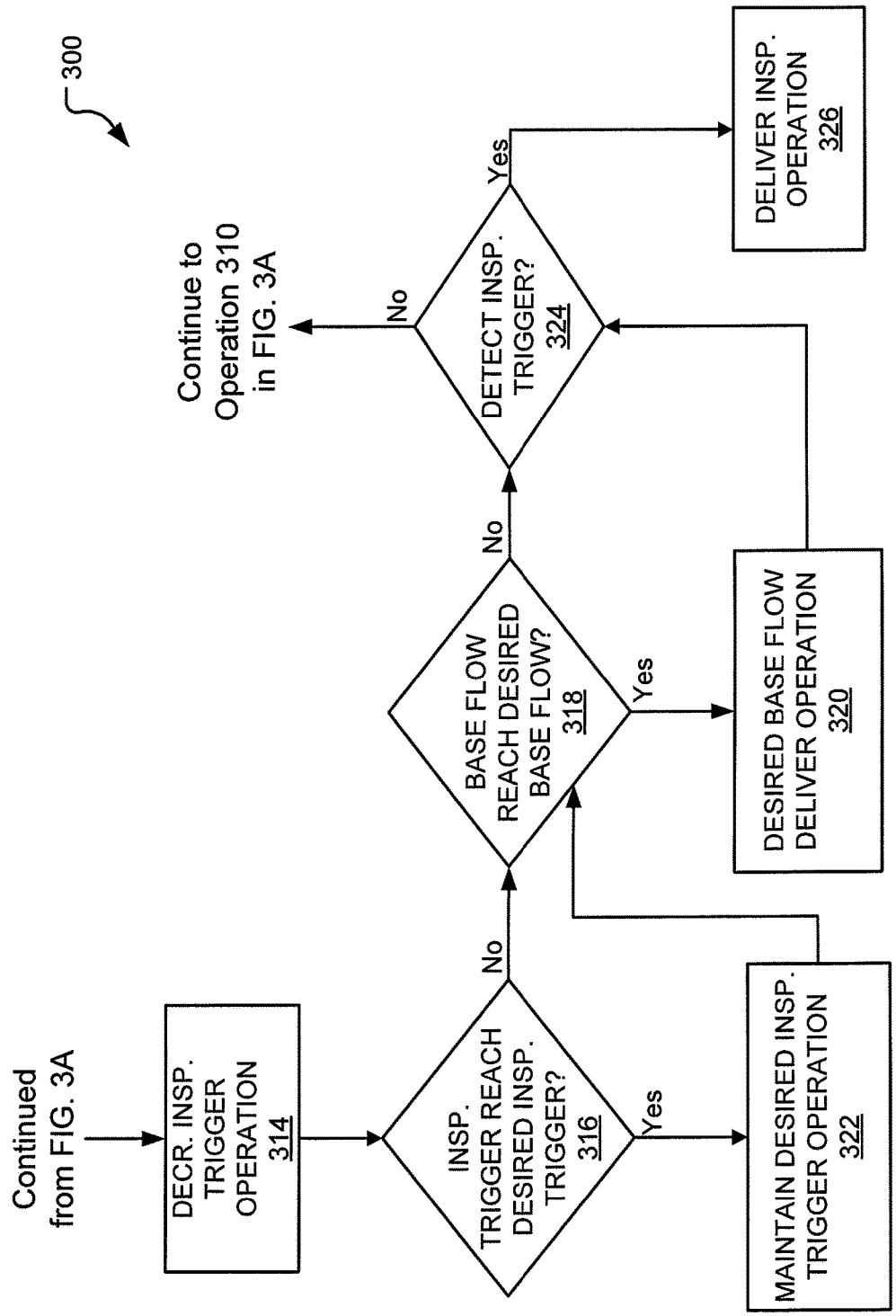
FIG. 3B illustrates an embodiment of a second portion of the method shown in FIG. 3A for ventilating a patient on a ventilator.

FIGS. 3A and 3B illustrate an embodiment of a method 300 for ventilating a patient with a ventilator. As illustrated, method 300 begins at the start of exhalation. As illustrated in FIG. 3A, method 300 includes an initial base flow deliver operation 302, determine initial inspiratory trigger threshold operation 303, decision operation 304 (illustrated as "Detect Initial Insp. Trigger"), decision operation 306 (illustrated as "Min. Exh. Time Expired?"), decision operation 308 (illustrated as "Max. Exh. Time Expired?"), and decision operation 312 (illustrated as "Exh. Flow less than Max. Exh. Flow?"). During the initial base flow deliver operation 302, the ventilator delivers an initial base flow to the patient during exhalation during at least a first portion of exhalation. During the initial base flow deliver operation 302, the ventilator performs determine initial inspiratory trigger threshold operation 303, decision operation 304, decision operation 306, decision operation 308, and decision operation 312.

The ventilator during the determine initial inspiratory trigger threshold operation 303, determines an initial inspiratory trigger threshold for the first portion of exhalation. In some embodiments, initial inspiratory trigger threshold is determined by the ventilator. In other embodiments, initial inspiratory trigger threshold is determined based on operator input or selection.

The ventilator during the decision operation 304 monitors patient and/or ventilator parameters to determine if an inspiratory trigger threshold has been met and/or exceeded during the first portion of exhalation. The inspiratory trigger threshold includes any suitable condition or threshold for determining that inspiration should be provided to the patient. During the first portion of exhalation, the inspiratory threshold includes the initial inspiratory trigger threshold as determined by determine initial inspiratory trigger threshold operation 303. For example, the initial inspiratory trigger threshold may require a change of pressure of at least 6 to 10 cm of $H_2O$.

In some embodiments, method 300 detects changes in a ventilator and/or patient parameter during the decision operation 304 via the monitoring of a respiratory gas pressure, the monitoring of lung flow, direct or indirect measurement of nerve impulses, or any other suitable method for detecting changes in a ventilator parameter for comparison to inspiratory trigger thresholds. Method 300 may utilize sensors to monitor the ventilator and/or patient parameters. Sensors may include any suitable sensing device as known by a person of skill in the art for a ventilator. In some embodiments, the inspiratory trigger threshold may be a change in exhalation pressure or a change in exhalation flow. In some embodiments, the sensors are located in the pneumatic system, the breathing circuit, and/or on the patient. In some embodiments, the ventilator monitors the exhalation flow and/or exhalation pressure every computational cycle (e.g., 2 milliseconds, 5 milliseconds, 10 milliseconds, etc.) during the delivery of exhalation to determine if the inspiratory trigger threshold has been met and/or exceeded.

The ventilator during decision operation 304 compares the output of the one or more sensors to at least one inspiratory trigger threshold. If the output meets and/or exceeds the one or more inspiratory trigger thresholds, the ventilator determines during decision operation 304 that an inspiratory trigger is detected. If the output does not meet the one or more inspiratory trigger thresholds, the ventilator determines during decision operation 304 that an inspiratory trigger is not detected. If the ventilator determines that the inspiratory trigger is detected during the decision operation 304, the ventilator selects to perform deliver inspiratory operation 326 (illustrated as "Deliver Insp. Operation"). If the ventilator determines that the inspiratory trigger is not detected during the decision operation 304, the ventilator selects to perform decision operation 306.

As illustrated in FIG. 3A, method 300 includes a deliver inspiration operation 326. The ventilator during deliver inspiration operation 326 delivers inspiration to the patient ending exhalation. The ventilator performs deliver inspiration operation 326 when a patient trigger is detected. The ventilator delivers an inspiration based on ventilator parameters, patient parameters, and/or input or selections from the operator. For example, the inspiration provided by the ventilator may be based on a selected breath type and/or mode of ventilation.

The ventilator during decision operation 306 determines if the minimum exhalation time has expired. As discussed above, the minimum exhalation time refers to a predetermined amount of time in which it is unlikely that a patient would desire to begin inspiration or would attempt to trigger an inspiration. If the ventilator determines that the minimum exhalation time has not expired during decision operation 306, the ventilator selects to perform decision operation 304. If the ventilator determines that the minimum exhalation time has expired during decision operation 306, the ventilator selects to perform decision operation 308. In some embodiments, the ventilator determines if the minimum exhalation time has expired by monitoring the output of sensors and/or by monitoring calculations based on the output of sensors.

The ventilator during decision operation 308 determines if the maximum exhalation time has expired. As discussed above, the maximum exhalation time refers to a predetermined amount of time after which it becomes highly likely that a patient would attempt to trigger inspiration. If the ventilator determines that the maximum exhalation time has not expired during decision operation 308, the ventilator selects to perform decision operation 312. If the ventilator determines that the maximum exhalation time has expired during decision operation 308, the ventilator selects to perform increasing base flow delivery operation 310 (illustrated as "Incr. Base Flow Deliver Operation). In some embodiments, the ventilator determines if the maximum exhalation time has expired by monitoring the output of sensors and/or by monitoring calculations based on the output of sensors.

The ventilator during decision operation 312 determines if the exhalation flow is below the minimum exhalation flow. In some embodiments, the ventilator determines the exhalation flow by monitoring the output of sensors and/or by monitoring calculations based on the output of sensors. The minimum exhalation flow refers to a predetermined flow rate that when exhaled by the patient indicates that a patient is approaching the end of active exhalation. In some embodiments, the minimum exhalation flow is zero. In some embodiments, the minimum exhalation flow is determined by the ventilator. In other embodiments, the minimum exhalation flow is set or determined by the operator via operator input or selection. If the ventilator determines that the exhalation flow is below the minimum exhalation flow during decision operation 312, the ventilator selects to perform increasing base flow delivery operation 310. If the ventilator determines that the exhalation flow is not below the minimum exhalation flow during decision operation 312, the ventilator selects to perform decision operation 304.

As further illustrated in FIG. 3A, method 300 includes an increasing base flow delivery operation 310 (illustrated as "Incr. Base Flow Deliver Operation). The ventilator during the increasing base flow delivery operation 310 increases the amount of base flow delivered to the patient during exhalation at an exponential trajectory from the initial base flow towards a desired base flow. The exponential trajectory is based on a constant. The constant is determined by the ventilator. In some embodiments, the desired base flow is determined by the ventilator. In other embodiments, the desired base flow is received by the ventilator via operator input or selection.

The increasing base flow delivery operation 310 is performed by the ventilator during at least a second portion of exhalation. During the increasing base flow delivery operation 310, the ventilator performs decreasing inspiratory trigger threshold operation 314 (illustrated as "Decr. Insp. Trigger Operation"), decision operation 316 (illustrated as "Insp. Trigger Reach Desired Insp. Trigger?"), decision operation 318 (illustrated as "Base Flow reach Desired Base Flow?"), and decision operation 324 (illustrated as "Detect Insp. Trigger?") as illustrated in FIG. 3B.

As illustrated in FIG. 3B, method 300 includes a decreasing inspiratory trigger threshold operation 314. The ventilator during the decreasing inspiratory trigger threshold operation 314 decreases the inspiratory trigger threshold monitored by the ventilator during exhalation at an exponential trajectory from the initial inspiratory trigger threshold towards a desired inspiratory trigger threshold. The exponential trajectory is based on the same constant as utilized by the ventilator during the increasing base flow delivery operation 310 to determine the base flow trajectory. In some embodiments, the desired inspiratory trigger threshold is determined by the ventilator. In other embodiments, the desired inspiratory trigger threshold is received by the ventilator via operator input or selection. As discussed above the ventilator performs decreasing inspiratory trigger threshold operation 314 while performing the increasing base flow delivery operation 310. In some embodiments, the increasing base flow delivery operation 310 is performed concurrently with the decreasing inspiratory trigger threshold operation 314 by the ventilator as illustrated in FIG. 4.

Method 300 includes a decision operation 316, decision operation 318, and decision operation 324. The order of the performance of the decision operation 316, the decision operation 318, and decision operation 324 is irrelevant. Accordingly, the decision operation 316, the decision operation 318, and decision operation 324 may be performed in any order, simultaneously, at different times, and/or at overlapping times. Further, the decision operation 316, the decision operation 318, and decision operation 324 are all performed during at least the second portion of exhalation.

The ventilator during decision operation 316 determines if the inspiratory trigger threshold has substantially reached the desired inspiratory threshold. The ventilator may determine if the inspiratory trigger threshold has substantially reached a desired inspiratory threshold. If the ventilator determines that the inspiratory trigger threshold has substantially reached the desired inspiratory threshold during decision operation 316, the ventilator selects to perform maintaining desired inspiratory trigger threshold operation 322 (illustrated as "Maintain Desired Insp. Trigger Operation"). If the ventilator determines that the inspiratory trigger threshold has not substantially reached the desired inspiratory threshold during decision operation 316, the ventilator selects to perform decision operation 318.

Further, method 300 includes a maintaining desired inspiratory trigger threshold operation 322. The ventilator during the maintaining desired inspiratory trigger threshold operation 322 sets and holds the inspiratory trigger threshold at the desired inspiratory trigger threshold. The performance of the maintaining desired inspiratory trigger threshold operation 322 ends the ventilator performance of the decreasing inspiratory trigger threshold operation 314.

The ventilator during decision operation 318 determines if the delivered base flow has substantially reached the desired base flow. The ventilator may determine if the base flow has substantially reached the desired base flow by monitoring the output of one or more sensors or by monitoring calculations based on the output of one or more sensors. If the ventilator determines that the base flow has substantially reached the desired base flow during decision operation 318, the ventilator selects to perform desired base flow deliver operation 320. If the ventilator determines that the base flow has not substantially reached the desired base flow during decision operation 318, the ventilator selects to perform decision operation 324. As discussed above, the desired inspiratory trigger threshold or the desired base flow is substantially reached when the ventilator can no longer increase the amount of base flow provided without reaching or exceeding the desired base flow or when ventilator can no longer decrease the inspiratory trigger threshold without reaching or exceeding the desired inspiratory trigger threshold based on the sensitivity and precision of the ventilator components.

As illustrated in FIG. 3B, method 300 includes a desired base flow deliver operation 320. The ventilator during the desired base flow deliver operation 320 sets and holds the base flow delivered to the patient during at the second portion of exhalation at the desired base flow. The performance of the desired base flow deliver operation 320 ends the ventilator performance of the increasing base flow delivery operation 310.

Method 300 includes a decision operation 324. The ventilator during the decision operation 324 monitors patient and/or ventilator parameters to determine if an inspiratory trigger threshold has been met and/or exceeded during the second portion of exhalation. The inspiratory trigger threshold includes any suitable condition or threshold for determining that inspiration should be provided to the patient. During the second portion of exhalation, the inspiratory trigger threshold includes the varying inspiratory trigger threshold as determined by decreasing inspiratory trigger threshold operation 314.

In some embodiments, method 300 detects changes in a ventilator and/or patient parameter during the decision operation 324 via the monitoring of a respiratory gas pressure, the monitoring of lung flow, direct or indirect measurement of nerve impulses, or any other suitable method for detecting changes in a ventilator parameter for comparison to inspiratory trigger thresholds. Method 300 may utilize sensors to monitor the ventilator and/or patient parameters. Sensors may include any suitable sensing device as known by a person of skill in the art for a ventilator. In some embodiments, the inspiratory trigger threshold may be a change in exhalation pressure or a change in exhalation flow. In some embodiments, the sensors are located in the pneumatic system, the breathing circuit, and/or on the patient. In some embodiments, the ventilator monitors the exhalation flow and/or exhalation pressure every computational cycle (e.g., 2 milliseconds, 5 milliseconds, 10 milliseconds, etc.) during the delivery of exhalation to determine if the inspiratory trigger threshold has been met and/or exceeded.

The ventilator during decision operation 324 compares the output of the one or more sensors to at least one inspiratory trigger threshold. If the output meets and/or exceeds the one or more inspiratory trigger threshold, the ventilator determines during decision operation 324 that an inspiratory trigger is detected. If the output does not meet the one or more inspiratory trigger thresholds, the ventilator determines during decision operation 324 that an inspiratory trigger is not detected. If the ventilator determines that the inspiratory trigger is detected during the decision operation 324, the ventilator selects to perform deliver inspiration operation 326 (illustrated as "Deliver Insp. Operation"). If the ventilator determines that the inspiratory trigger is not detected during the decision operation 324, the ventilator selects to perform increasing base flow delivery operation 310 as illustrated in FIG. 3A.

In some embodiments, method 300 includes an estimating operation and an adjusting operation. The ventilator during the estimating operation estimates the amount of flow leaked from a ventilation tubing system during ventilation. The ventilator may utilize any known methods for estimating the amount of flow leaked from the ventilation tubing system. The ventilator during the adjusting operation adds the estimated amount of leak flow to the initial base flow to account for the amount of flow leaked from the ventilation tubing system. Further, the ventilator during the adjusting operation may add the estimated amount of leak flow to a desired base flow to account for the amount of flow leaked from the ventilation tubing system.

In other embodiments, method 300 includes a display operation. The ventilator during the display operation displays any suitable information for display on a ventilator. In one embodiment, the display operation displays at least one of a minimum exhalation flow, a minimum exhalation time, a maximum exhalation time, a desired base flow, a desired inspiratory trigger threshold, an inspiratory trigger threshold, a base flow, an exhalation flow, an estimated leak flow, and an exhalation pressure.

Method 300 decreases the inspiratory trigger threshold while the base flow is being adjusted since the longer the exhalation period, the more likely the patient will attempt to initiate an inspiratory trigger. The decrease in the inspiratory trigger threshold allows a patient to exert less effort to trigger a desired inspiration during the second portion of exhalation as it becomes more likely that a patient will attempt to trigger an inspiration.

Further, method 300 allows the ventilator to reduce the amount of base flow delivered during exhalation. The smaller the ventilator-delivered base flow is during active exhalation, the smaller the uncertainty contributed by measuring base flow by different sensors (once on the delivery side and a second time as a portion of exhaust gas on the exhalation side). This is particularly advantageous under neonatal conditions when tidal volumes and exhaled flow rates are relatively smaller and may be some orders of magnitude smaller than the base flow. Accordingly, method 300 allows the ventilator to more accurately calculate exhaled tidal volume and/or spirometry than ventilators that utilize a constant base flow or a higher amount of base-flow during active exhalation.

Accordingly, in some embodiments, method 300 includes a calculation operation. The ventilator during the calculation operation calculates an exhaled tidal volume. The ventilator may utilize any known methods for calculating exhaled tidal volume. In some embodiments, the ventilator during the calculation operation also calculates spirometry. In some embodiments, the spirometry calculation is based on the calculated exhaled tidal volume. The ventilator may utilize any known methods for calculating spirometry.

In other embodiments, a microprocessor-based ventilator that accesses a computer-readable medium having computer-executable instructions for performing the method of ventilating a patient with a ventilator is disclosed. This method includes repeatedly performing the steps disclosed in method 300 above and/or as illustrated in FIG. 3.

EXAMPLES

Example 1

FIG. 4 illustrates an embodiment of a graph of delivered base flow and an inspiratory trigger threshold over time during an exhalation. According to this embodiment, a base flow change is executed at the beginning of the exhalation phase. In this embodiment, the desired inspiratory trigger threshold is 3 LPM and the desired base flow is 4.5 LPM. In this embodiment, the first portion of exhalation ends upon the occurrence of a condition, which starts the second portion of exhalation. According to the illustrated embodiment, the condition occurs at 350 milliseconds (ms). The condition may include determining that a minimum exhalation time has expired, determining that an exhalation flow is below the minimum exhalation flow, determining that the exhalation flow is below the minimum exhalation flow prior to expiration of a maximum exhalation time, and/or determining that the maximum exhalation time has expired.

In an embodiment as illustrated in FIG. 4, an initial inspiratory trigger threshold of 10 LPM is set during the first portion of exhalation. As illustrated in FIG. 4, an initial base flow of 1.5 LPM is delivered during the first portion of exhalation. After the occurrence of the condition and during the second portion of exhalation, as illustrated in FIG. 4, the inspiratory trigger threshold is decreased exponentially while the delivered base flow is increased exponentially to reach 4.5 LPM. The inspiratory trigger threshold is decreased until the set inspiratory trigger threshold reaches the desired inspiratory trigger threshold (3 LPM). Once the inspiratory trigger threshold reaches the desired inspiratory trigger threshold, the inspiratory trigger threshold is maintained at the desired inspiratory trigger threshold. Further, the delivered base flow is increased until the delivered base flow reaches the desired base flow. Once the delivered base flow reaches the desired base flow, the delivered base flow is maintained at the desired base flow.

A patient initiated inspiration is not detected during the exhalation time shown in FIG. 4. If an inspiratory trigger was detected, inspiration would be delivered upon detection ending the exhalation period.

Example 2

Example 2 illustrates an embodiment of a pseudo code for the systems and methods of the disclosure. The pseudo code illustrated below utilizes an algorithm that incorporates the following aspects:

1) Base flow is initiated after the flow rate being exhaled by the patient has reduced to a minimum threshold, which indicates that a patient is approaching the end of active exhalation;
2) Base flow will be delivered in accordance with an exponential trajectory to reach a desired base flow within an optimum interval to both maintain Positive End-Expiratory Pressure (PEEP) and to minimize false triggering; and
3) An inspiratory trigger threshold will be adaptively adjusted (with an exponential trajectory) from a less sensitive threshold (i.e., harder to trigger) at the start of exhalation phase and decreasing smoothly to asymptote to a desired inspiratory trigger threshold by the end of active exhalation or after allowing an optimum interval concomitant with reaching the final base flow.

The pseudo code embodiment utilizing the algorithm described above is listed below:

```
//initialize
filteredSensEx (inspiratory trigger threshold) = 10.0 LPM
//calculate a new base flow reference:
leakAdd = estimated Value (estimated leak from the ventilator tubing system);
DesiredFlow = BaseFlow + leakAdd;
MinQE (minimum exhalation flow) = 1.5 LPM;
MinTE (minimum exhalation time) = 150 ms;
Alpha (a constant) = 0.05;
MaxTE (maximum exhalation time) = 500 ms;
//every control cycle during exhalation phase execute the following.
```

```
IF (neonatal)
{
    IF (ExhTime < MinTE)
    {
        DesiredFlow = leakAdd;
        BaseFlowCheck = false;
        filteredBaseFlow = 0;
Sensitivity = setSensitivity+filteredSensEx;
}
Else
{   IF (((Qexh < MinQE) AND (!BaseFlowCheck)) OR (exhTime > MaxTE))
        BaseFlowCheck = true;
}
    IF (BaseFlowCheck)
        {
            filteredBaseFlow = filteredBaseFlow * (1-alpha) + alpha * baseFlow;
            DesiredFlow = filteredBaseFlow + leakAdd;
            Sensitivity = setSensitivity + filteredSenEx * (1-alpha);
            filteredSensEx = filteredSensEx * (1-alpha)
        }
    Else
{
        DesiredFlow = leakAdd;
    }
}
// no change if Adult or Pediatric settings.
```

Example 3

Example 3 illustrates an embodiment of a pseudo code for the systems and methods of the disclosure. The pseudo code illustrated below utilizes an algorithm that incorporates the following aspects:
1) Base flow is initiated and regulated based on a current estimate of the leak rate as exemplified above;
2) An increase in leak rate is detected requiring adjustment of base flow; and
3) An inspiratory trigger threshold will be adaptively adjusted (with an exponential trajectory) smoothly to asymptote to a desired inspiratory trigger threshold by the end of transition period or after allowing an optimum interval concomitant with reaching the final base flow.

The pseudo code embodiment utilizing the algorithm described above is listed below upon detecting a change in leak rate:

```
//initialize
filteredSensEx (inspiratory trigger threshold) = 5.0 LPM
//calculate new base flow and sensitivity references:
OldLeakAdd = previous estimated Value (estimated leak from the ventilator tubing system);
NewLeakAdd = current estimated Value (updated estimated leak);
filteredBaseFlow = BaseFlow +OldLeakAdd;
DesiredBaseFlow = BaseFlow +NewLeakAdd;
Sensitivity = setSensitivity+filteredSensEx;
Alpha (a constant) = 0.05;
//Upon detecting a change in leak rate during exhalation and doing the
initialization above, perform the following every control cycle.
IF (Exhalation)
{
    filteredBaseFlow = filteredBaseFlow * (1-alpha) + alpha * NewBaseFlow;
    DesiredBaseFlow = filteredBaseFlow;
    Sensitivity = setSensitivity + filteredSenEx * (1-alpha);
    filteredSensEx = filteredSensEx * (1-alpha);
}
```

The pseudo code provided above is not meant to be limiting. Further, while values are provided in the embodiment of the pseudo code above, these values are not meant to be limiting and may vary based on ventilator and/or patient parameters.

Those skilled in the art will recognize that the methods and systems of the present disclosure may be implemented in many manners and as such are not to be limited by the foregoing exemplary embodiments and examples. In other words, functional elements being performed by a single or multiple components, in various combinations of hardware and software or firmware, and individual functions, can be distributed among software applications at either the client or server level or both. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software firmware components described herein as would be understood by those skilled in the art now and hereafter.

Numerous other changes may be made which will readily suggest themselves to those skilled in the art and which are encompassed in the spirit of the disclosure and as defined in the appended claims. While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the claims.

What is claimed is:

1. A method for ventilating a patient with a ventilator during an exhalation of the patient, the method comprising:
    delivering a base flow as an initial base flow to the patient during a first portion of the exhalation, the initial base flow based on an estimated leak flow;
    determining a change in the estimated leak flow;
    based on the change in the estimated leak flow, during the first portion of the exhalation, progressively adjusting the base flow, according to a first exponential trajectory, from the initial base flow to an adjusted base flow and progressively adjusting an inspiratory trigger threshold from an initial inspiratory trigger threshold to an adjusted inspiratory trigger threshold;
    identifying a transition condition to transition to a second portion of the exhalation associated with a desired base flow and a desired trigger threshold;
    based on the desired base flow, during the second portion of the exhalation, changing the base flow from the adjusted base flow toward the desired base flow; and
    based on the desired trigger threshold, during the second portion of the exhalation, changing the inspiratory trigger threshold from the adjusted inspiratory trigger threshold toward the desired trigger threshold.

2. The method of claim 1, wherein progressively adjusting the inspiratory trigger threshold during the first portion of the exhalation is adjusted based on the first exponential trajectory.

3. The method of claim 1, wherein changing the base flow during the second portion of the exhalation includes changing the base flow according to a second exponential trajectory.

4. The method of claim 1, wherein changing the inspiratory trigger threshold during the second portion of the exhalation is based on a second exponential trajectory.

5. The method of claim 1, wherein identifying the transition condition is associated with one or more of: an amount of time or an exhalation flow.

6. The method of claim 1, wherein the determined change in the estimated leak flow is an increase in the estimated leak flow, and wherein the step of progressively adjusting the base flow and the inspiratory trigger threshold includes progressively increasing the inspiratory trigger threshold as a function of the increase in the estimated leak flow.

7. The method of claim 1, wherein progressively adjusting the initial base flow and progressively adjusting the inspiratory trigger threshold are performed concurrently.

8. The method of claim 1, wherein no change in the estimated leak flow is determined during the second portion of exhalation.

9. The method of claim 1, wherein the change in the estimated leak flow is a first change, the method further comprising:
   determining a second change in the estimated leak flow during the second portion of the exhalation; and
   based on the second change in the estimated leak flow, progressively adjusting the base flow and the inspiratory trigger threshold during the second portion of exhalation.

10. The method of claim 9, wherein progressively adjusting the base flow and the inspiratory trigger threshold during the second portion of exhalation happens concurrently with changing the base flow and the inspiratory trigger threshold.

11. A ventilator for ventilating a patient during an exhalation of the patient, comprising:
   a display;
   a processor;
   memory storing instructions that, when executed by the processor, cause the ventilator to perform a set of operations comprising:
      delivering a base flow as an initial base flow to the patient during a first portion of the exhalation, the initial base flow based on an estimated leak flow and associated with an initial inspiratory trigger threshold;
      identifying a transition condition to transition to a second portion of the exhalation associated with a desired base flow and a desired trigger threshold;
      based on the desired base flow, during the second portion of the exhalation, changing the base flow from the initial base flow toward the desired base flow according to an exponential trajectory;
      based on the desired trigger threshold, during the second portion of the exhalation, changing an inspiratory trigger threshold from the initial inspiratory trigger threshold toward the desired trigger threshold;
      determining a change in the estimated leak flow; and
      based on the change in the estimated leak flow, during the second portion of exhalation, progressively adjusting the base flow and the inspiratory trigger threshold while changing the base flow and the inspiratory trigger threshold.

12. The ventilator of claim 11, the set of operations further comprising:
   displaying, at the display, at least one of: a minimum exhalation flow, a minimum exhalation time, a maximum exhalation time, the desired base flow, the desired trigger threshold, the inspiratory trigger threshold, the base flow, an exhalation flow, the estimated leak flow, the determined change in the estimated leak flow, and an exhalation pressure.

13. The ventilator of claim 11, wherein, during the second portion of the exhalation, changing the base flow and changing the inspiratory trigger threshold are each based on the exponential trajectory.

14. The ventilator of claim 13, wherein a slope of the exponential trajectory is based on a time constant selected by the ventilator.

15. The ventilator of claim 13, the ventilator further comprising a sensor, and wherein the set of operations further comprise:
   calculating an estimated exhaled tidal volume of the patient, based on an output from the sensor.

16. The ventilator of claim 11, wherein progressively adjusting the base flow and inspiratory trigger threshold occurs over a time period spanning at least two control cycles of the ventilator.

17. The ventilator of claim 11, wherein progressively adjusting the base flow and the inspiratory trigger threshold includes at least one of: phases, a step-wise pattern, or an exponential trajectory.

18. A ventilator configured to perform a method of ventilating a patient with the ventilator, the method comprising:
   delivering a base flow as an initial base flow to the patient during a first portion of exhalation, the initial base flow based on an estimated leak flow;
   determining a first change in the estimated leak flow, during the first portion of the exhalation;
   based on the first change in the estimated leak flow, during the first portion of the exhalation, progressively adjusting, according to an exponential trajectory, the base flow from the initial base flow to an adjusted base flow and progressively adjusting an inspiratory trigger threshold from an initial inspiratory trigger threshold to an adjusted inspiratory trigger threshold;
   identifying a transition condition to transition to a second portion of the exhalation associated with a desired base flow and a desired trigger threshold;
   based on the desired base flow, during the second portion of the exhalation, changing the base flow from the adjusted base flow toward the desired base flow;
   based on the desired trigger threshold, during the second portion of the exhalation, changing the inspiratory trigger threshold from the adjusted inspiratory trigger threshold toward the desired trigger threshold;
   determining a second change in the estimated leak flow during the second portion of the exhalation; and
   based on the second change in the estimated leak flow, progressively adjusting the base flow and the inspiratory trigger threshold.

19. The ventilator of claim 18, the method further comprising:
   detecting, during the second portion of exhalation, that a patient parameter is greater than or equal to the inspiratory trigger threshold; and
   based on the patient parameter being greater than or equal to the inspiratory trigger threshold, ending the exhalation of the patient.

* * * * *